(12) United States Patent
Sheffer

(10) Patent No.: US 9,381,047 B2
(45) Date of Patent: Jul. 5, 2016

(54) INTERSPINOUS IMPLANT

(75) Inventor: Garrett Austin Sheffer, Hoboken, NJ (US)

(73) Assignee: EBI, LLC, Parsippany, NJ (US)

( * ) Notice: Subject to any disclaimer, the term of this patent is extended or adjusted under 35 U.S.C. 154(b) by 949 days.

(21) Appl. No.: 12/899,079

(22) Filed: Oct. 6, 2010

(65) Prior Publication Data
US 2011/0040330 A1 Feb. 17, 2011

Related U.S. Application Data

(63) Continuation-in-part of application No. 11/746,204, filed on May 9, 2007, now Pat. No. 9,173,686.

(51) Int. Cl.
*A61B 17/70* (2006.01)

(52) U.S. Cl.
CPC ......... *A61B 17/7062* (2013.01); *A61B 17/7067* (2013.01); *A61B 17/7068* (2013.01)

(58) Field of Classification Search
CPC .............. A61F 2/4405; A61B 17/7062; A61B 17/7067; A61B 17/7068
USPC .............................. 606/248, 249; 623/17.13
See application file for complete search history.

(56) References Cited

U.S. PATENT DOCUMENTS

| | | | |
|---|---|---|---|
| 5,314,477 A | 5/1994 | Marnay | |
| 5,645,599 A | 7/1997 | Samani | |
| 5,683,464 A | 11/1997 | Wagner et al. | |
| 6,139,579 A | 10/2000 | Steffee et al. | |
| 6,238,397 B1 | 5/2001 | Zucherman et al. | |
| 6,293,949 B1 | 9/2001 | Justis et al. | |
| 6,419,676 B1 | 7/2002 | Zucherman et al. | |
| 6,440,169 B1 | 8/2002 | Elberg et al. | |
| 6,626,943 B2 | 9/2003 | Eberlein et al. | |
| 6,743,257 B2 | 6/2004 | Castro | |

(Continued)

FOREIGN PATENT DOCUMENTS

| EP | 1330987 A1 | 7/2003 |
|---|---|---|
| EP | 1945117 A2 | 7/2008 |

(Continued)

OTHER PUBLICATIONS

Partial European Search Report (R.64 EPC) mailed Aug. 25, 2008 for European Patent Application No. EP 08251646.

(Continued)

*Primary Examiner* — Brian Pellegrino
(74) *Attorney, Agent, or Firm* — Schwegman Lundberg & Woessner, P.A.

(57) ABSTRACT

An interspinous implant is provided. The interspinous implant can include a first member having a first end and a second end. At least one of the first end and the second end can include a mating portion. The interspinous implant can also include a second member, which can have a first end, a second end and at least one receiving portion formed adjacent to at least one of the first end and the second end. The at least one receiving portion can receive the mating portion to couple the first member to the second member at a desired orientation. The interspinous implant can also include a first extension, which can be substantially opposite the mating portion, and adapted to engage a spinous process. The interspinous implant can comprise a second extension, which can be substantially opposite the at least one receiving portion, and adapted to engage a second process.

13 Claims, 30 Drawing Sheets

(56) References Cited

U.S. PATENT DOCUMENTS

| | | |
|---|---|---|
| 6,761,719 B2 | 7/2004 | Justis et al. |
| 7,011,685 B2 | 3/2006 | Arnin et al. |
| 7,108,697 B2 | 9/2006 | Mingozzi et al. |
| 7,497,859 B2 | 3/2009 | Zucherman et al. |
| 2004/0002708 A1* | 1/2004 | Ritland ............ 606/61 |
| 2004/0106995 A1 | 6/2004 | Le Couedic et al. |
| 2005/0125063 A1 | 6/2005 | Matge et al. |
| 2005/0131412 A1 | 6/2005 | Olevsky et al. |
| 2005/0203624 A1 | 9/2005 | Serhan et al. |
| 2005/0261768 A1 | 11/2005 | Trieu |
| 2005/0273100 A1 | 12/2005 | Taylor |
| 2006/0015181 A1 | 1/2006 | Elberg |
| 2006/0084988 A1 | 4/2006 | Kim |
| 2006/0085070 A1 | 4/2006 | Kim |
| 2006/0149278 A1 | 7/2006 | Abdou |
| 2006/0184171 A1 | 8/2006 | Biedermann et al. |
| 2006/0271049 A1 | 11/2006 | Zucherman et al. |
| 2006/0293662 A1* | 12/2006 | Boyer et al. ............ 606/61 |
| 2007/0032790 A1 | 2/2007 | Aschmann et al. |
| 2007/0106298 A1 | 5/2007 | Carli et al. |
| 2007/0161992 A1 | 7/2007 | Kwak et al. |
| 2007/0161993 A1 | 7/2007 | Lowery et al. |
| 2007/0162000 A1 | 7/2007 | Perkins |
| 2007/0162001 A1 | 7/2007 | Chin et al. |
| 2007/0162002 A1 | 7/2007 | Tornier |
| 2007/0162003 A1 | 7/2007 | Tornier et al. |
| 2007/0162004 A1 | 7/2007 | Tornier et al. |
| 2007/0162005 A1 | 7/2007 | Peterson et al. |
| 2007/0191837 A1 | 8/2007 | Trieu |
| 2007/0225706 A1 | 9/2007 | Clark et al. |
| 2007/0233076 A1 | 10/2007 | Trieu |
| 2007/0260245 A1 | 11/2007 | Malandain et al. |
| 2007/0265623 A1 | 11/2007 | Malandain et al. |
| 2007/0276373 A1 | 11/2007 | Malandain |
| 2007/0282340 A1 | 12/2007 | Malandain |
| 2008/0147192 A1 | 6/2008 | Edidin et al. |
| 2008/0161818 A1 | 7/2008 | Kloss et al. |
| 2008/0255668 A1 | 10/2008 | Fallin et al. |
| 2008/0262622 A1 | 10/2008 | Butler |
| 2008/0281423 A1 | 11/2008 | Sheffer et al. |
| 2008/0294200 A1 | 11/2008 | Kohm et al. |
| 2009/0012528 A1 | 1/2009 | Aschmann et al. |
| 2009/0054988 A1 | 2/2009 | Hess |
| 2009/0054989 A1 | 2/2009 | Baumgartner et al. |
| 2009/0234389 A1 | 9/2009 | Chuang et al. |
| 2009/0254122 A1 | 10/2009 | Khalife |
| 2009/0264927 A1 | 10/2009 | Ginsberg et al. |
| 2009/0265006 A1 | 10/2009 | Seifert et al. |
| 2009/0270919 A1 | 10/2009 | Dos Reis, Jr. |

FOREIGN PATENT DOCUMENTS

| | | | |
|---|---|---|---|
| EP | 1994901 A1 | 11/2008 | |
| WO | WO-2006110578 | 10/2006 | |
| WO | WO-2007134113 | 11/2007 | |
| WO | WO-2008136877 A1 | 11/2008 | |
| WO | WO 2009036156 A1 * | 3/2009 | ............ A61B 17/70 |

OTHER PUBLICATIONS

Non-Final Office Action for U.S. Appl. No. 11/746,204 Mailed Jul. 6, 2011.

* cited by examiner

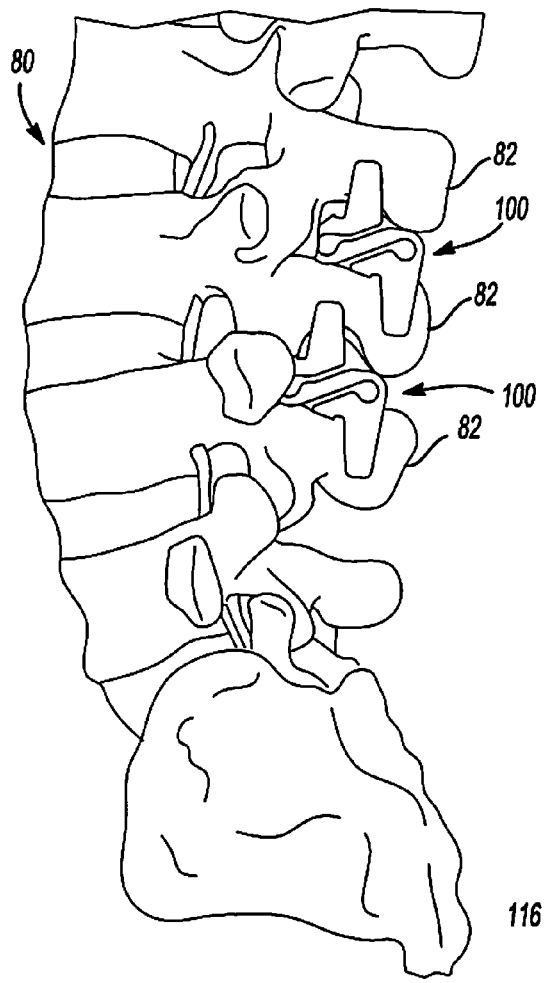
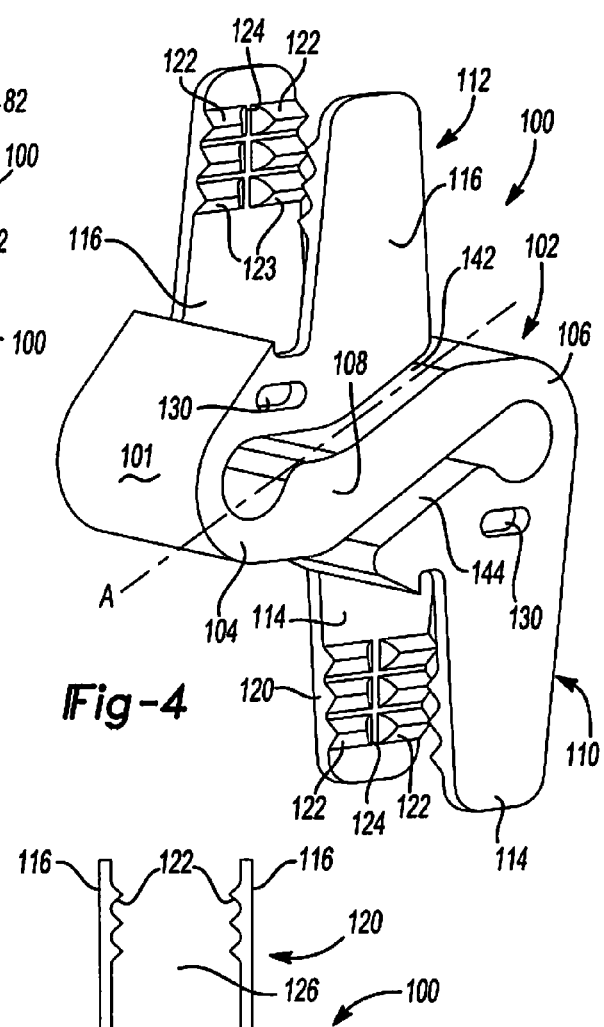
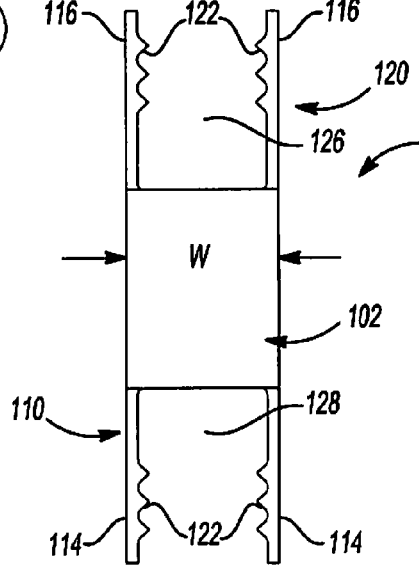
Fig-3
Fig-4
Fig-5

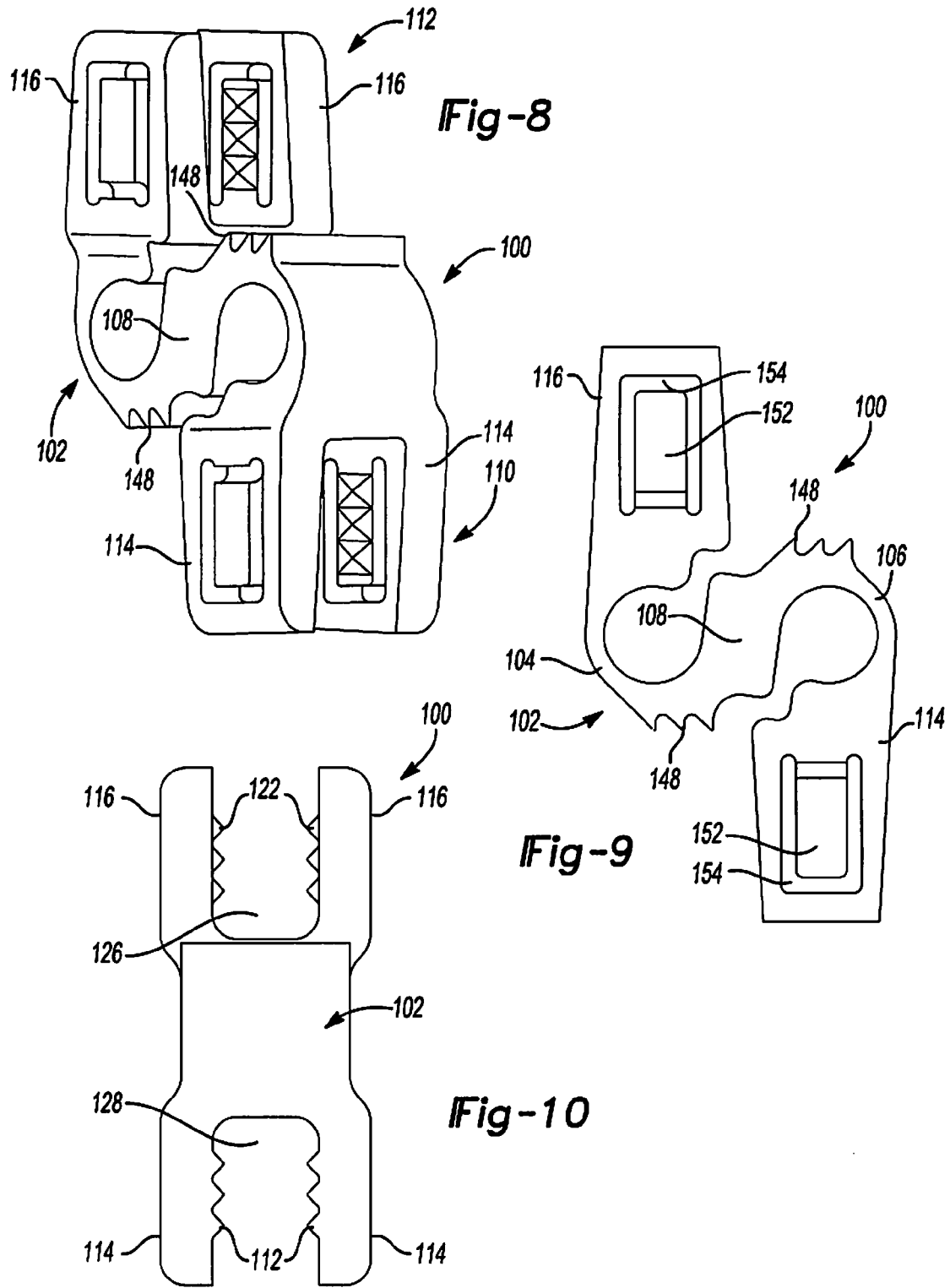

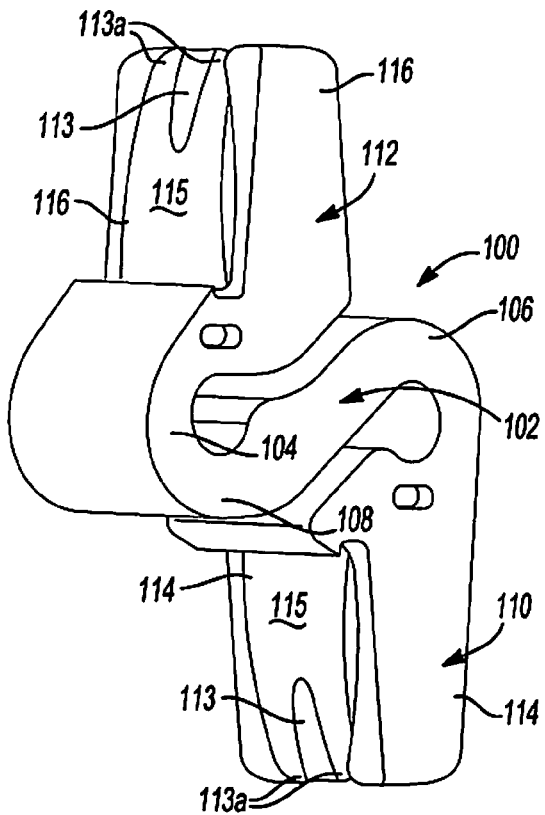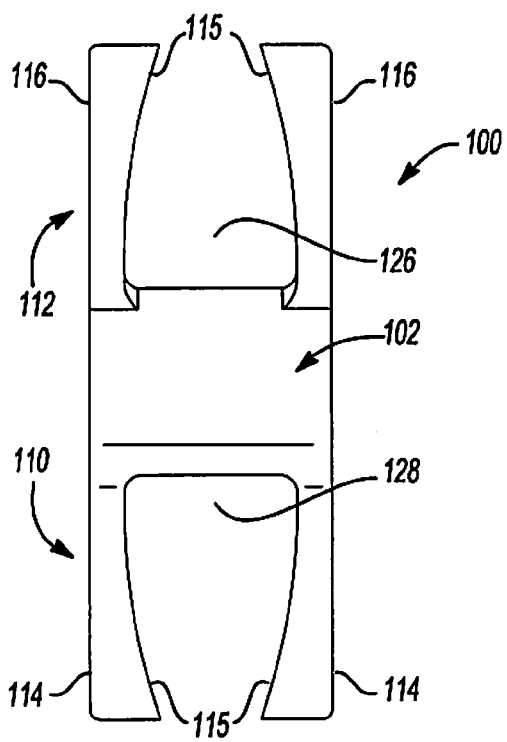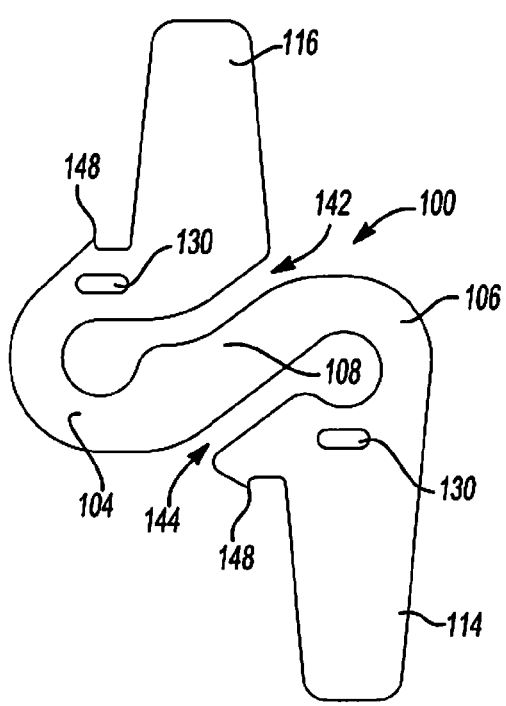
Fig-13
Fig-13A
Fig-13B

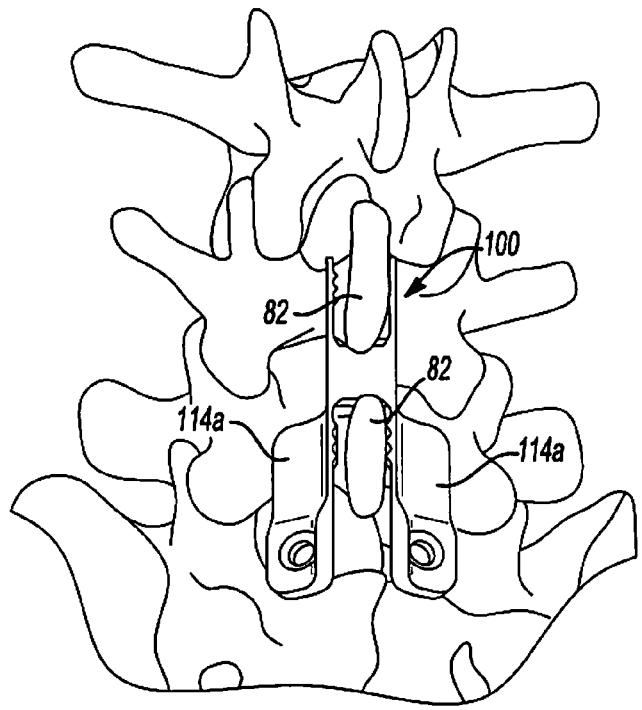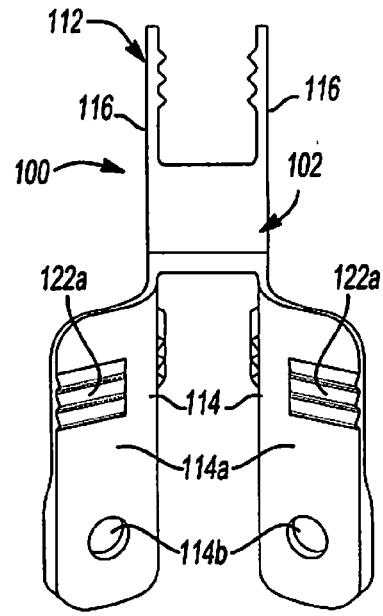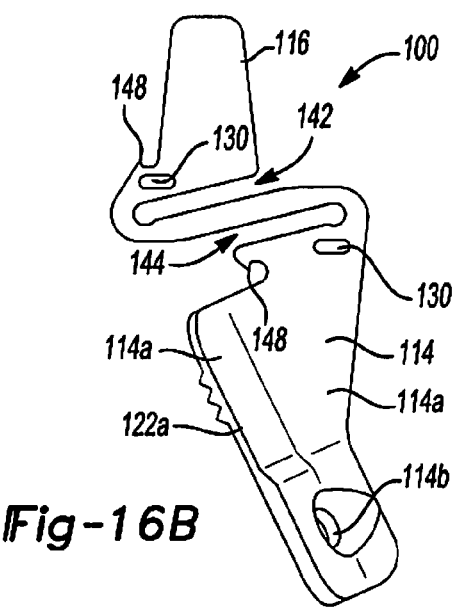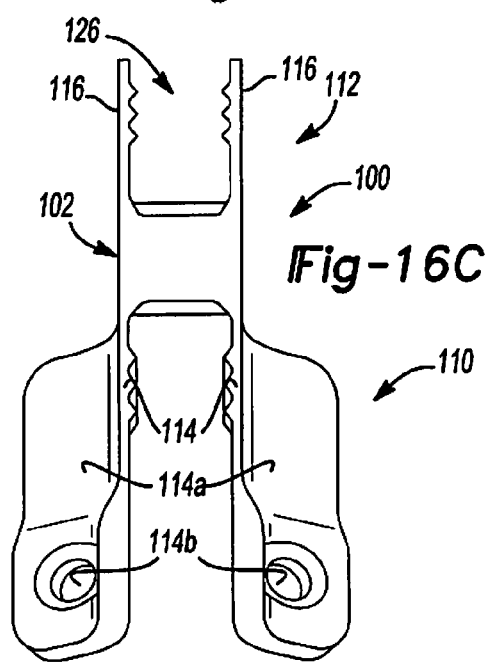
Fig-16
Fig-16A
Fig-16B
Fig-16C

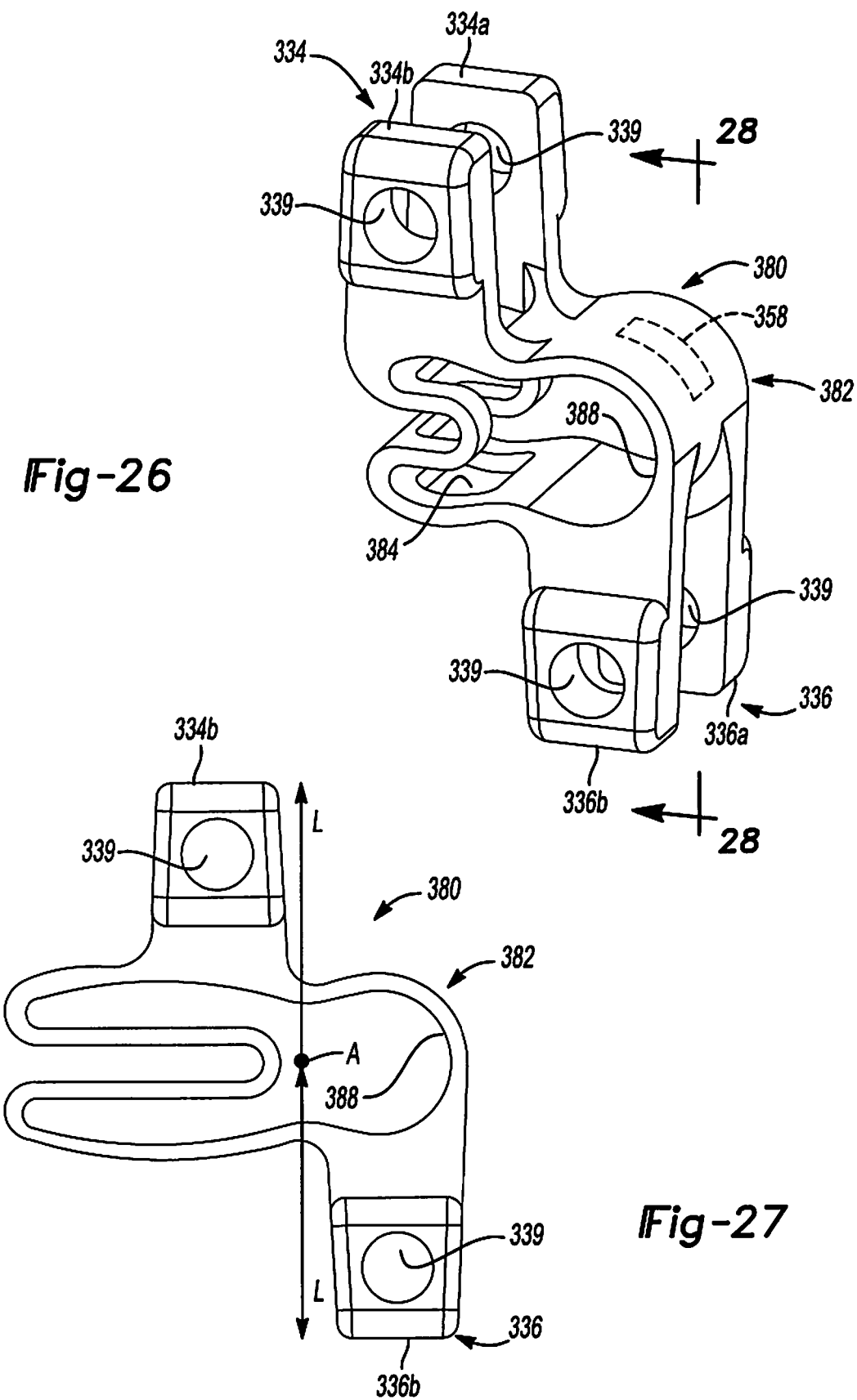

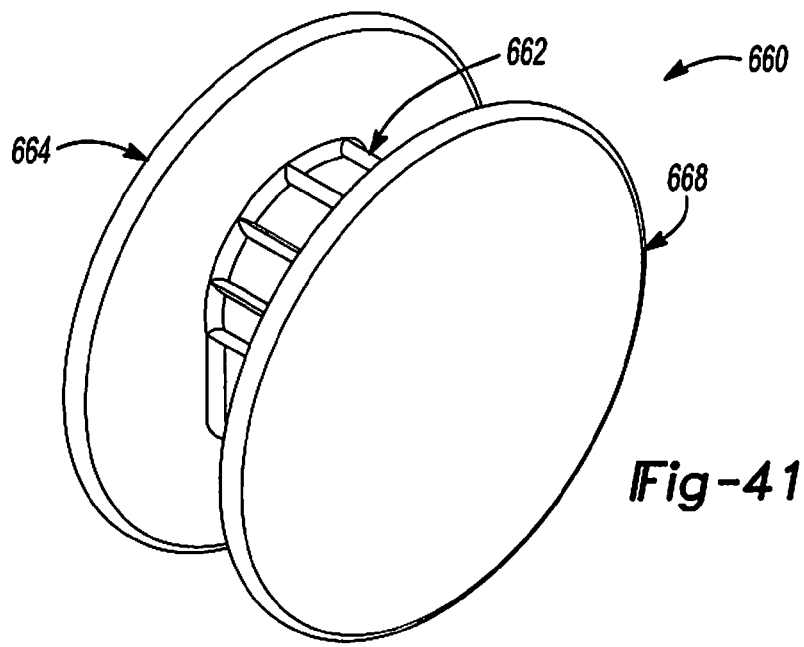
Fig-41
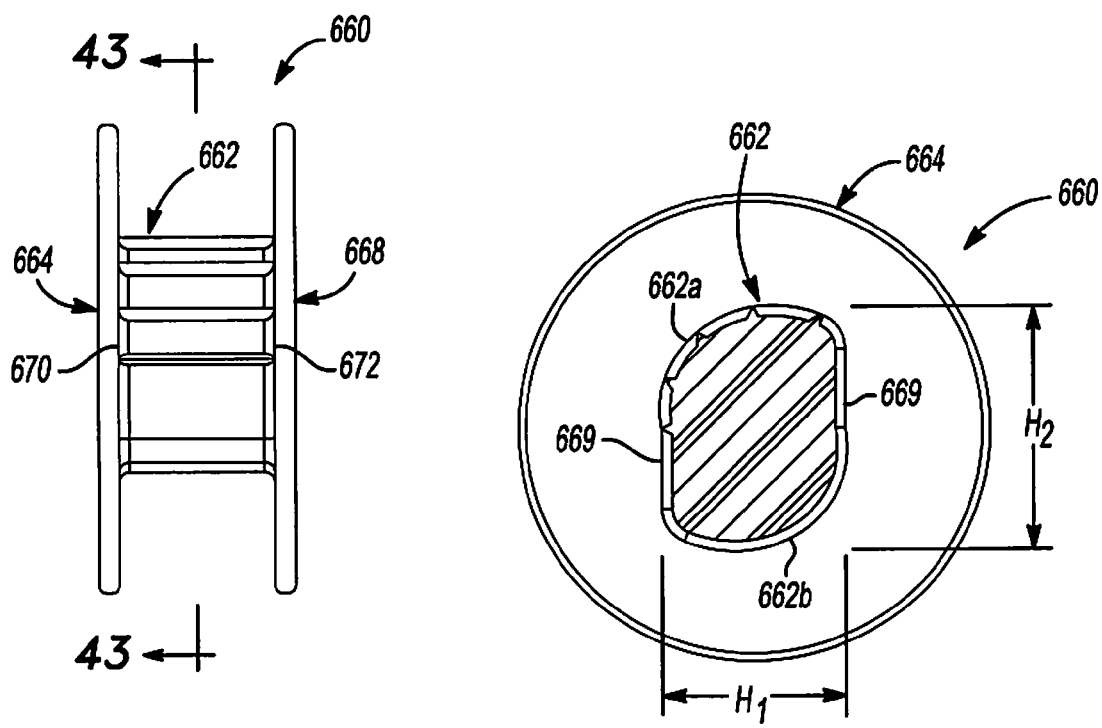
Fig-42
Fig-43

INTERSPINOUS IMPLANT

CROSS-REFERENCE TO RELATED APPLICATIONS

This application is a continuation-in-part of U.S. patent application Ser. No. 11/746,204, filed on May 9, 2007. The entire disclosure of the above application is incorporated herein by reference.

INTRODUCTION

Various interspinous implants are known for correcting damaged intervertebral disks or other conditions that can subject the spinous processes of adjacent vertebrae to stresses, overextension; painful wear and tear, or general instability of the spinal column.

The present teachings provide an interspinous implant that can stabilize the spine and limit overextension of the spine and excessive spacing between the superior and inferior processes.

SUMMARY

The present teachings provide an interspinous implant that includes a substantially S-shaped body having a longitudinal anterior-posterior axis and first and second ends, a first U-shaped extension attached to the first end, and a second U-shaped extension attached to the second end. The first and second extensions can be oriented at an angle relative to the anterior-posterior axis and engageable to first and second spinous processes. The second extension can be offset relative to the first extension along the anterior-posterior axis. In one aspect, the S-shaped body can be resilient and can include a first portion having first and second ends and being substantially U-shaped, a second portion having first and second ends and being substantially U-shaped and an intermediate portion connecting the second end of the first portion and the first end of the second portion The present teachings also provide an interspinous implant that includes a resilient S-shaped body including first and second saddle-shaped portions, and first and second stirrup-shaped brackets extending at an angle and in opposite directions from the first and second saddle-shaped portions. The first and second stirrup-shaped brackets can engage first and second spinous processes.

Also provided is an interspinous implant defining a longitudinal axis. The interspinous implant can include a first member having a first end and a second end. At least one of the first end and the second end can include a mating portion. The interspinous implant can also include a second member. The second member can have a first end, a second end and at least one receiving portion formed adjacent to at least one of the first end and the second end. The at least one receiving portion can receive the mating portion to couple the first member to the second member at a desired orientation. The interspinous implant can also include a first extension, which can be coupled to the first member substantially opposite the mating portion. The first extension can be adapted to engage a first spinous process. The interspinous implant can comprise a second extension, which can be coupled to the second member substantially opposite the at least one receiving portion. The second extension can be adapted to engage a second spinous process.

Further provided is an interspinous implant defining a longitudinal axis. The interspinous implant can include a body having a first end opposite a second end. Each of the first end and the second end can include a mating portion. The interspinous implant can also comprise a first extension, which can have at least one slot formed opposite a first channel to receive the mating portion of the first end. The first channel can be adapted to engage a first spinous process. The interspinous implant can include a second extension, which can have at least one slot formed opposite a second channel to receive the mating portion of the second end. The second channel can be adapted to engage a second spinous process. Each of the at least one slot of the first extension and the at least one slot of the second extension can be formed at an angle relative to the longitudinal axis such that when the first extension and second extension are coupled to the body, the body lies in a plane substantially transverse to the longitudinal axis.

Also provided is an interspinous spacer defining a longitudinal axis, which includes a first member. The first member can have a first end and a second end. The first end and the second end can each include a mating portion. The interspinous implant can also include a second member, which can have a first end, a second end and a plurality of receiving portions formed adjacent to the first end and the second end that receive a respective one of the mating portions to couple the first member to the second member. The interspinous implant can include a first U-shaped extension coupled to the first member substantially opposite the mating portions. The first U-shaped extension can be adapted to engage a first spinous process. The interspinous implant can also include a second U-shaped extension coupled to the second member substantially opposite the plurality of receiving portions. The second U-shaped extension can be adapted to engage a second spinous process. The first member can be coupled to the second member such that the first U-shaped extension is laterally offset from the second U-shaped extension.

Further areas of applicability of the present teachings will become apparent from the description provided hereinafter. It should be understood that the description and specific examples are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 3 is a side view of two interspinous implants according to the present teachings, the interspinous implants shown implanted in a spine;

FIG. 4 is a perspective view of an interspinous implant according to the present teachings;

FIG. 5 is a rear view of the interspinous implant of FIG. 4;

FIG. 8 is a perspective view of an interspinous implant according to the present teachings;

FIG. 9 is a side view of the interspinous implant of FIG. 8;

FIG. 10 is a rear view of the interspinous implant of FIG. 8;

FIG. 13 is a perspective view of an interspinous implant according to the present teachings;

FIG. 13A is a rear view of the interspinous implant of FIG. 13;

FIG. 13B is a side view of the interspinous implant of FIG. 13;

FIG. 16 is an environmental view of an interspinous implant according to the present teachings, the interspinous implant shown implanted in a spine;

FIG. 16A is a rear view of the interspinous implant of FIG. 16;

FIG. 16B is a side view of the interspinous implant of FIG. 16;

FIG. 16C is a front view of the interspinous implant of FIG. 16;

FIG. 26 is a perspective illustration of an exemplary interspinous implant according to various teachings;

FIG. 27 is a side view of the interspinous implant of FIG. 26;

FIG. 41 is a perspective illustration of an exemplary interspinous implant according to various teachings;

FIG. 42 is a side view of the interspinous implant of FIG. 41;

FIG. 43 is a cross-sectional illustration of the interspinous implant of FIG. 41, taken along line 43-43 of FIG. 42;

DESCRIPTION OF VARIOUS ASPECTS

The following description is merely exemplary in nature and is in no way intended to limit the present teachings, applications, or uses. The present teachings generally provide an interspinous implant that can be used to limit overextension of the spine and provide normal motion. Further, the interspinous implant can stabilize the posterior spinous processes and promote fusion of the vertebral bodies. The present teachings can be used to provide interspinous implants for procedures intended to alleviate conditions resulting from damaged intervertebral disks, spinal stenosis or other conditions that can subject the spinous processes of adjacent vertebrae to stresses, overextension, painful wear and tear, or general instability of the spinal column. According to the present teachings, the interspinous implant can be used at any level of the spine, including, but not limited to L5-S1 levels.

Figure 1:
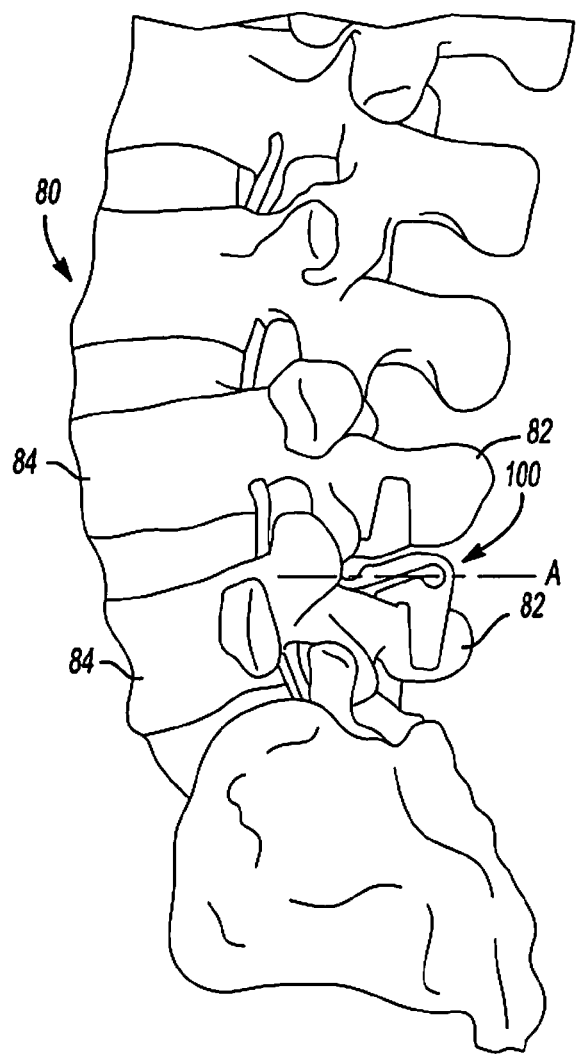
FIG. 1 is a side view of an interspinous implant according to the present teachings, the interspinous implant shown implanted in a spine.
Figure 2:
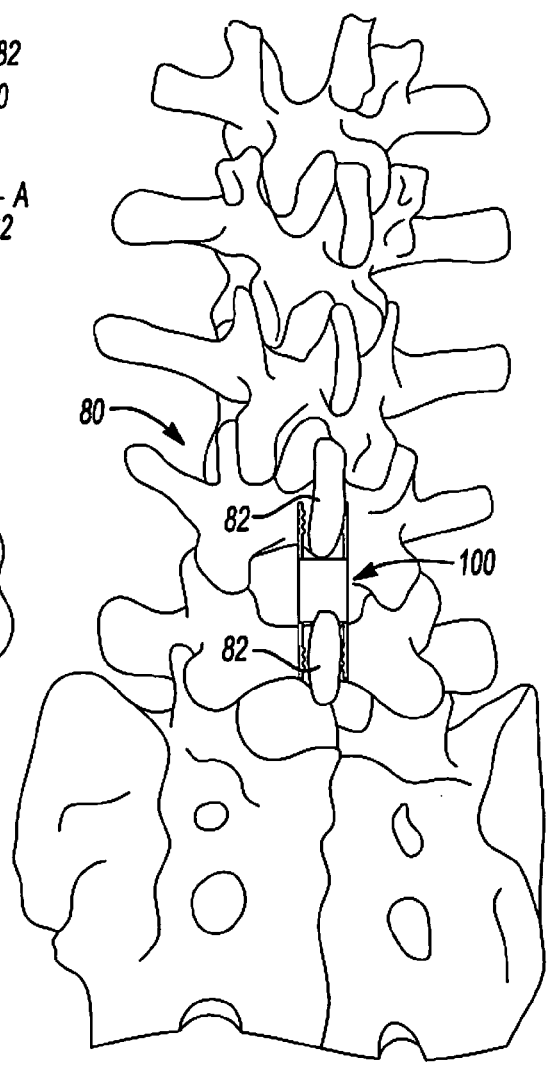
FIG. 2 is a rear view of the interspinous implant of FIG. 1, the interspinous implant shown implanted in a spine.

Referring to FIGS. 1 and 2, an exemplary interspinous implant 100 according to the present teachings is illustrated as implanted between two spinous processes 82 of adjacent or contiguous vertebrae 84 of a spine 80. It will be appreciated that one or more interspinous implants 100 can be used, as determined by the surgeon. Referring to FIG. 3, for example, two interspinous implants 100 are illustrated as implanted in a spine 80. It should be noted, however, that multiple interspinous implants 100 could be employed in a single surgical procedure, such as in the case of a multiple level procedure.

Referring to FIGS. 4-14C, and 16-17B, the interspinous implant 100 can include a body 102, and first and second extensions or brackets 112, 110. The body 102 can include first and second substantially U-shaped or saddle-shaped portions 104, 106 connected to one another by an intermediate portion 108. The first and second portions 104, 106 are oriented on opposite sides of the intermediate portion 108 along an axis A, in an opposing or antagonizing fashion, such that the body 102 can be substantially S-shaped. The body 102 can be made to be resilient such that the body 102 can operate as a tension spring, as discussed below. It should be understood, however, that the body 102 could be made rigid for use in a fusion spinal procedure. Upon implantation, the axis A of the body 102 is oriented in the anterior-posterior direction, as shown in FIG. 1, such that spine loads can be distributed over both first and second U-shaped portions 104, 106, thereby reducing by about half the load carried by each portion 104, 106.

The first extension 112, or the second extensions 110, or both extensions 112, 110 can be either fixedly or modularly connected to the body 102. The modular connection can be, for example, a taper connection, a dovetail connection, a snap fit connection, or other modular-type connection that allows easy removal of the corresponding first or second extension 112, 110 for minimally invasive insertion.

In another aspect, the first and second extensions 110, 112 can be movably connected to the body 102, such that the first and second extensions 110, 112 can be moved to a compact configuration for inserting the interspinous implant 100 into the spine. For example, the first and second extensions 110, 112 can be connected to the body 102 by pins received in corresponding elongated apertures or slots formed through the first and second extensions 112, 110. Translational movement of the first and second extensions 110, 112 relative to the body 102, with the pins sliding along the corresponding slots, can collapse the first and second extensions 110, 112 relative to the body 102 into a compact configuration. In another example, the first and second extensions 110, 112 can be rotatably coupled to the body 102, with hinges, pivots, living hinges, etc., for example. The first and second extensions 110, 112 can be rotated relative to the body 102 to a compact configuration for inserting the interspinous implant 100 into the spine.

In another aspect, one of the first or second extensions 112, 110 can be omitted. For example, the inferior extension 110 can be omitted and the body 102 can be formed as curved member that can act as an extension stop that does not limit flexion. Various fasteners, including screws, bolts, sutures, polyurethane suture cable, or cables can pass through openings, such as holes or elongated slots or other apertures provided through the first and second extensions 112, 110 or the body 102, for securing the interspinous implant 100 to the spinous process 82. Alternatively, the cables could be woven directly into the interspinous implant 100.

Figure 6:
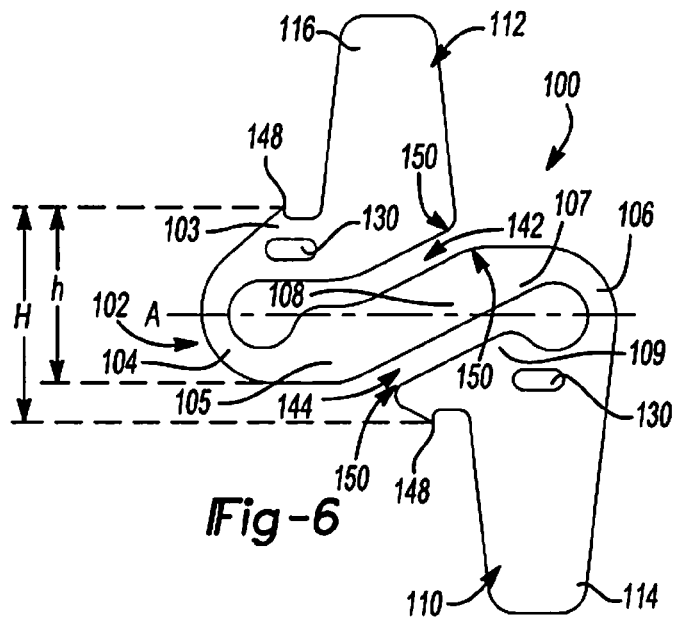
FIG. 6 is a side view of the interspinous implant of FIG. 4, shown in a first configuration.
Figure 6A:
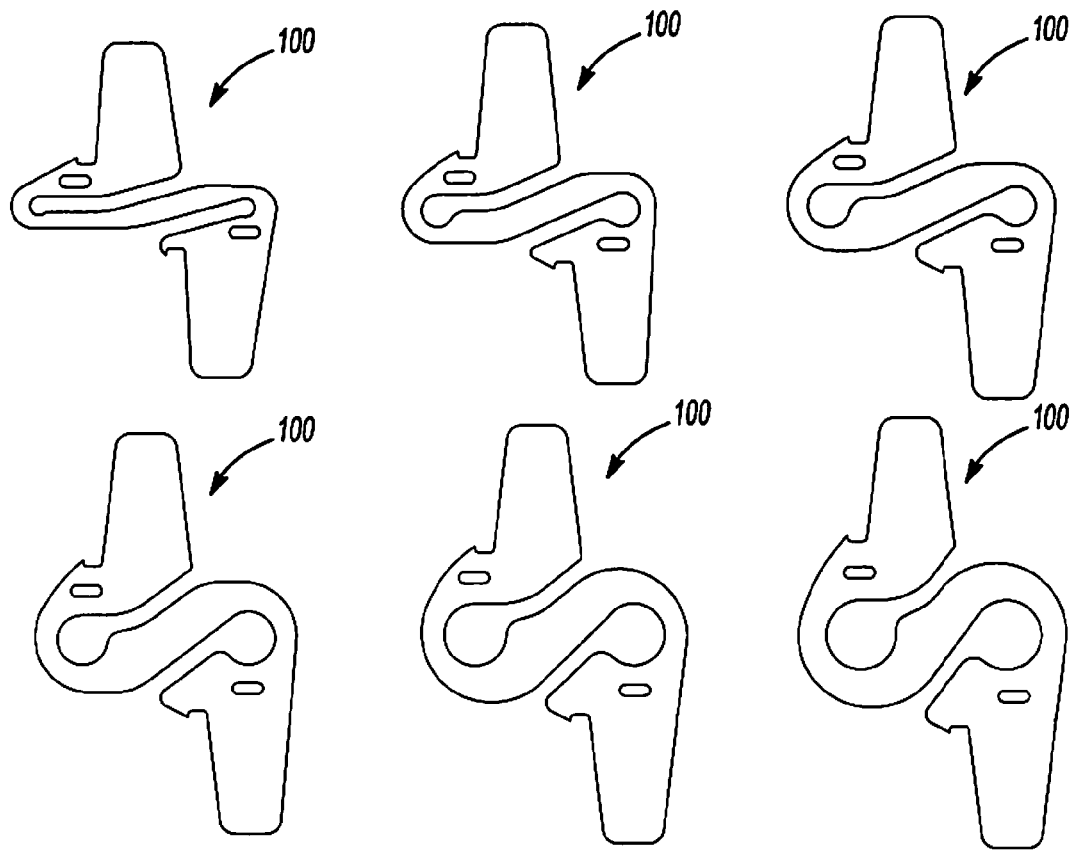
FIG. 6A illustrates side views of a series of representative interspinous implants according to the present teachings.

Referring to FIGS. 6 and 6A, exemplary sizes and shapes of the intervertebral implant 100 are illustrated. Referring to FIG. 6, for example, the first U-shaped portion 104 can include first and second ends 103, 105, and the second U-shaped portion 106 can include first and second ends 107, 109. The intermediate portion 108 can connect the second end 105 of the first portion 104 to the first end 107 of the second portion 106. The first and second extensions 112, 110 can extend substantially perpendicularly or at another angle relative to the axis A from the first and second ends 103, 109 of the first and second portions 104, 106 respectively.

The first and second extensions 112, 110 can be in the form of stirrup-shaped brackets for receiving corresponding adjacent spinous processes 82. The first extension 112 can include a pair of tabs or legs 116 defining an opening 126 for receiving a first spinous process 82. Each leg 116 can include anti-slip formations 122 for supporting, or engaging as needed, the spinous process 82. The anti-slip formations 122 can be in the form of series of sagittal teeth that may be interrupted by a coronal break 124 defining two columns 123, as illustrated in FIG. 4. Similarly, the second extension 110 can include a pair of tabs or legs 114 defining an opening 128 for receiving a second spinous process 82. Each leg 114 can include anti-slip formations 122 for supporting or engaging the spinous process 82. In one aspect, and in particular when the interspinous implant 100 is made of metal, such as titanium, shape memory metal or other biocompatible metal, the first and second extensions 112, 110 can be crimped onto to the corresponding spinous processes 82 for engaging the spinous processes 82. The first and second extensions 112, 110 can also be fastened with screws or bolts or other fasteners on the spinous processes.

Figure 7:
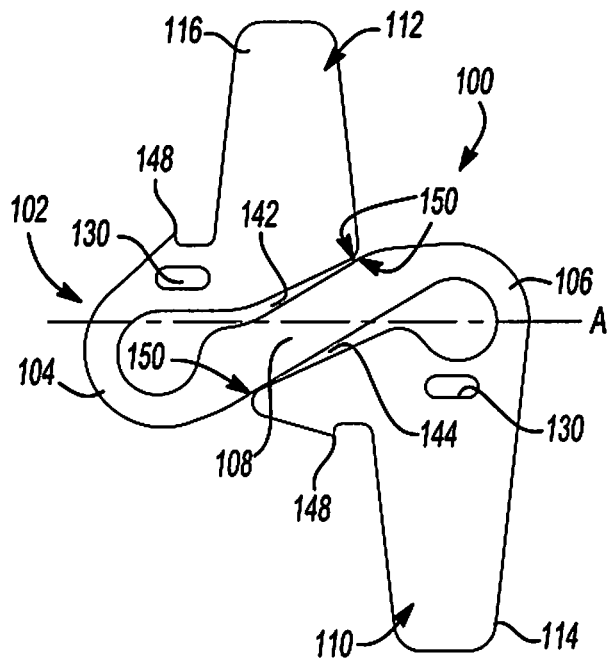
FIG. 7 is a side view of the interspinous implant of FIG. 4, shown in a third configuration.
Figure 7A:
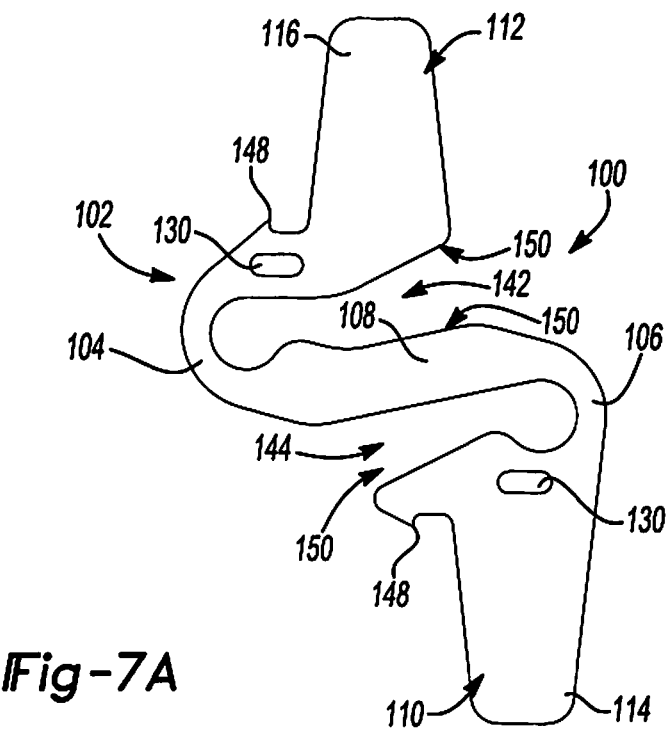
FIG. 7A is a side view of the interspinous implant of FIG. 4, shown in a second configuration.
Figure 11:
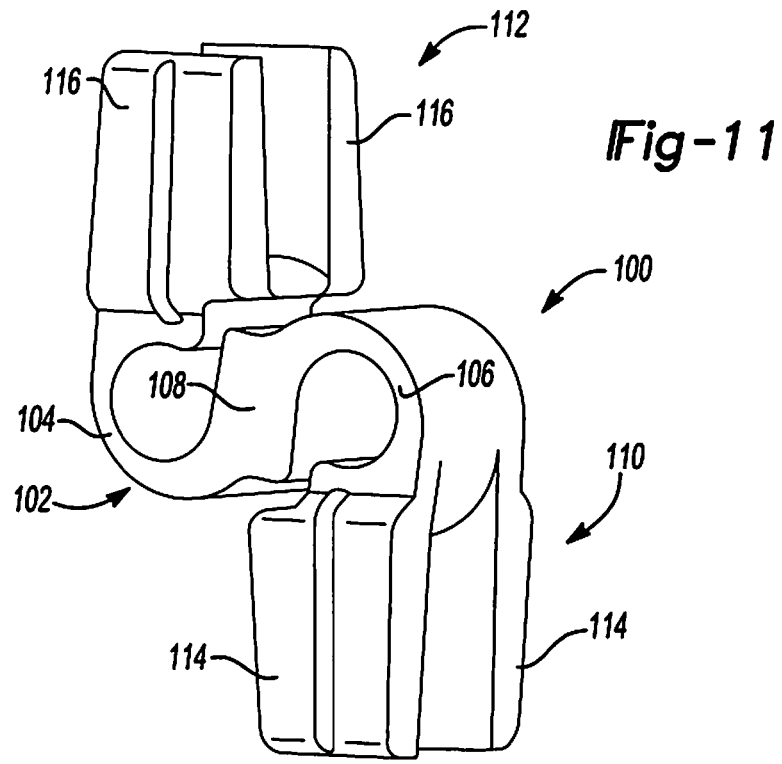
FIG. 11 is a perspective view of an interspinous implant according to the present teachings.
Figure 12:
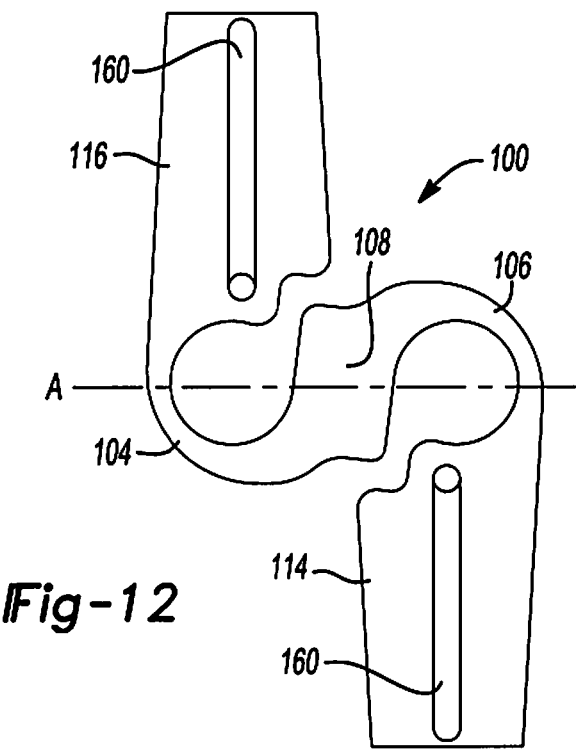
FIG. 12 is a side view of the interspinous implant of FIG. 11.

Referring to FIGS. 6, 7 and 7A, the geometry and construction of the body 102 can allow the body 102 to move between several configurations, including a first undeformed (or expanded) configuration, shown in FIG. 6, a second deformed and closed or collapsed configuration, shown in FIG. 7 and a third deformed and expanded configuration, shown in FIG. 7A. The first and second U-shaped portions 104, 106 can define corresponding first and second channels or gaps 142, 144 relative to the intermediate portion 108. The first and second channels 142, 144 can extend parallel to each other and oblique to the longitudinal axis of the implant 100 along at least portions of respective lengths thereof. In the undeformed configuration, the first and second channels 142, 144 can remain completely open with open end portions 150, as shown in FIG. 6, such that each channel 142, 144 forms an open loop. In the deformed and closed configuration, the end portions 150 of the first and second channels 142, 144 can close, as shown in FIG. 7, such that each channel 142, 144 forms a closed loop. In the deformed and open configuration the first and second channels 142, 144 can remain completely open and the end portions 150 can diverge further from the undeformed configuration, as shown in FIG. 7A. Accordingly, the end portions 150 can effectively define positive safety stops that prevent over-compression of the resilient body 102 and corresponding overextension of the spine 80 posteriorly, and also can limit fatigue loads and fatigue failure of the intervertebral implant 100.

The thickness or shape and size of the body 102 can be determined such that the body 102 only deforms elastically in a spring-like fashion and plastic deformation is avoided. For example, the intermediate portion 108 can have increased thickness relative to the first and second U-shaped portions 104, 106, and the body 102 can be shaped such that forces can be distributed through the thicker intermediate portion 108 or equally through the first and second portions 104, 106. Generally, the thickness and shape of the body 102 can vary, as shown in FIG. 6A, such that different motion characteristics or rigidity can be provided. The force distributing and resiliency characteristics of the body 102 can allow use of biocompatible materials that have modulus more similar to bone than titanium and other metals, including, for example, PEEK, or other biocompatible polymeric materials in addition to metals.

An exemplary interspinous implant 100 constructed from PEEK is illustrated in FIGS. 13, 13A and 13B. Instead of discrete anti-slip formations, the profile of the legs 116, 114 of the first and second extensions 112, 110 of the interspinous implant of FIG. 13 can be modified such that each leg 116, 114 can have a curved inner surface 115, and the corresponding leg 116, 114 has a thickness that increases away from the body 102. Each inner surface 115 can curve distally toward the curving surface 115 of the opposing leg 116, 114 of its corresponding extension 112, 110. Accordingly, the corresponding openings 126, 128 between the pair of legs 116, 114 can decrease away from the body 102, as shown in FIG. 13. In this manner, the first and second extensions 112, 110 can form scallop-like clips that can clamp onto the spinous processes 82 without crimping. The curved surfaces 115 can optionally include a relieved portion 113 defining teeth 113a for better fixation. In this regard, the teeth 113a can apply a constant clamping pressure, with a potential to remodel bone around the interspinous implant 100, thus providing better or increased fixation.

The body 102 can also include superior and inferior teeth or other superior and inferior engagement formations 148 for better fixation in the spine and resistance to expulsion, as shown in FIGS. 4 and 8, for example. In one aspect, the first U-shaped portion 104 of the body 102 can define an anterior surface 101 protruding into the vertebral foramen, such that the load on the disc space may be reduced, as shown in FIGS. 1 and 4. In addition, in the case of a spinal fusion procedure, one or more grafts could be placed through or within U-shaped portion 104 of the body 102 to facilitate bone ingrowth.

Referring to FIGS. 8-10, each leg 116, 114 of the first and second extensions 112, 110 can have a U-shaped opening or channel 154 defining a cantilevered or overhanging flange 152 that can operate as a resilient spring or clip for engaging the spinous processes 82 and allowing passage of a cable, ligament, graft or suture. In another aspect, referring to FIGS. 11 and 12, each leg 116, 114 of the first and second extensions 112, 110 can include a longitudinal through-groove 160 substantially perpendicular or at another angle relative to the axis A of the body 102. The longitudinal groove 160 can provide an access space for a cable, suture or other graft and can also reduce the thickness of each leg 116, 114 and increase the resilience of the first and second extensions 112, 110.

Figure 14:
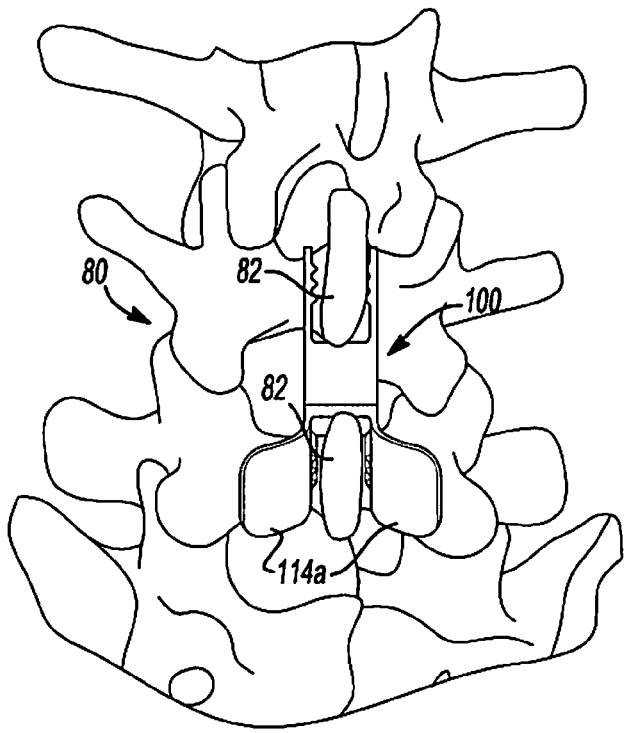
FIG. 14 is an environmental view of an interspinous implant according to the present teachings, the interspinous implant shown implanted in a spine.
Figure 14A:
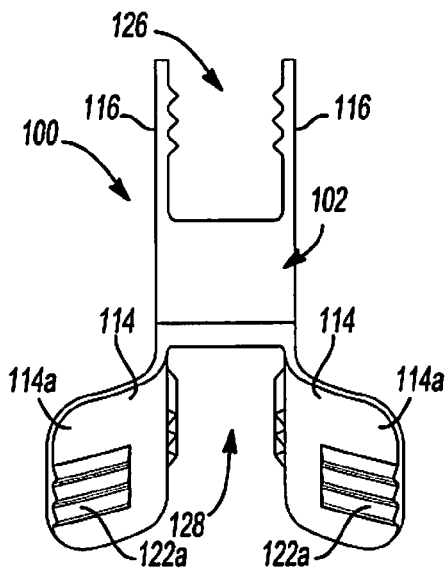
FIG. 14A is a rear view of the interspinous implant of FIG. 14.
Figure 14B:
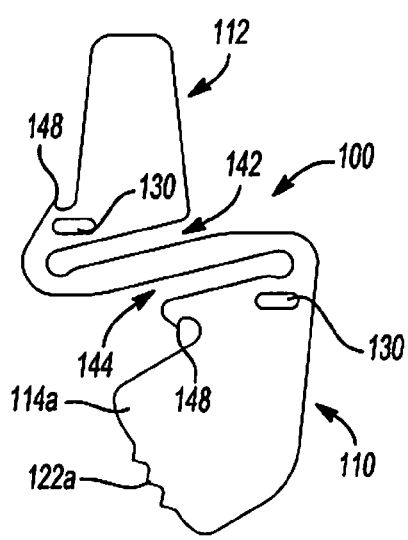
FIG. 14B is a side view of the interspinous implant of FIG. 14.
Figure 14C:
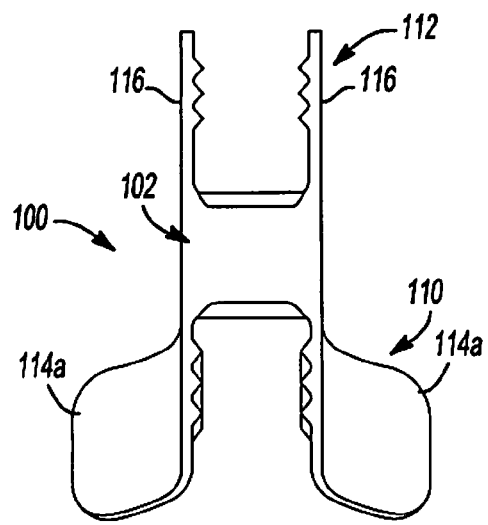
FIG. 14C is a front view of the interspinous implant of FIG. 14.
Figure 17A:
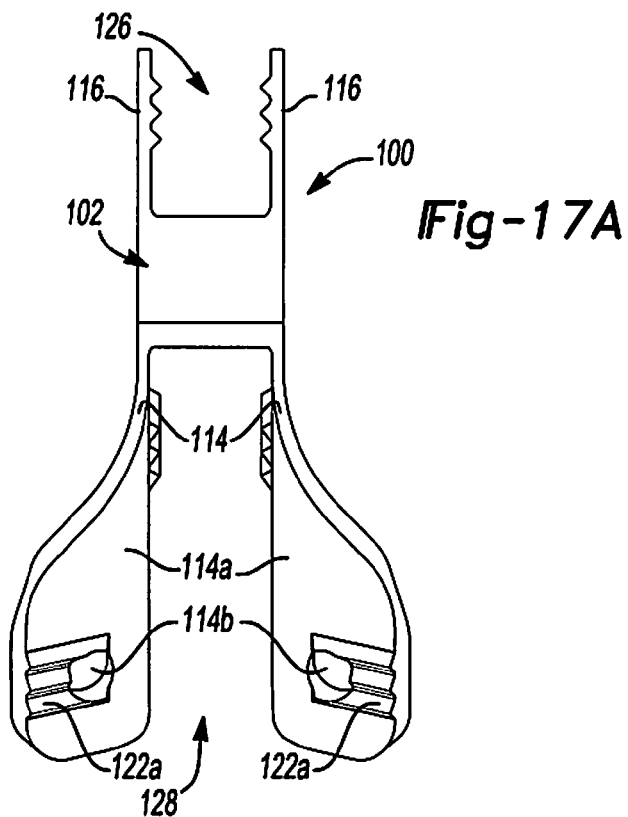
FIG. 17A is rear view of an interspinous implant according to the present teachings.
Figure 17B:
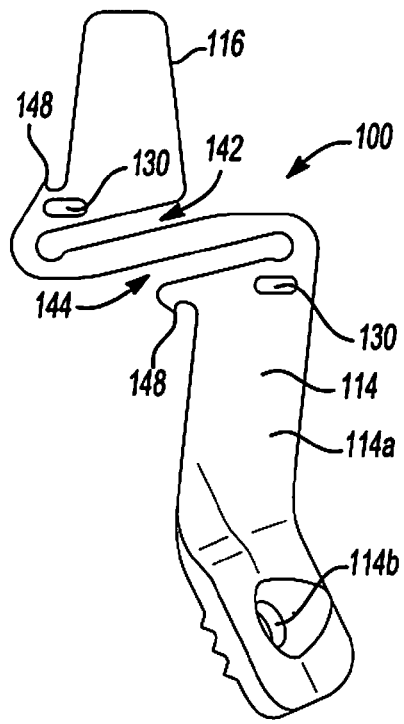
FIG. 17B is a side view of the interspinous implant of FIG. 17.
Figure 17C:
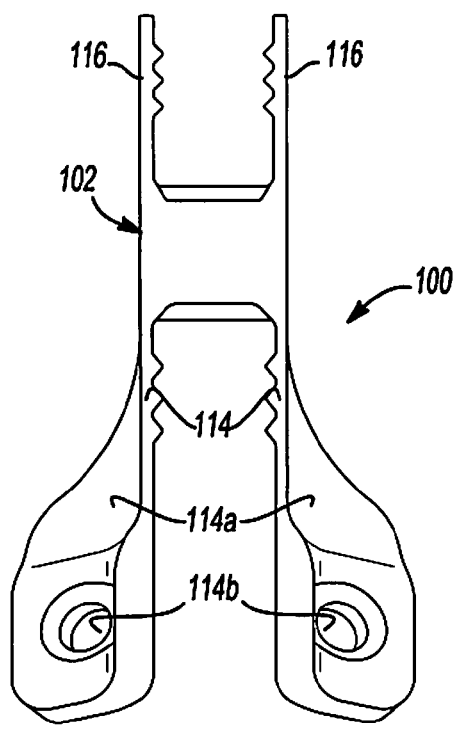
FIG. 17C is a front view of the interspinous implant of FIG. 17.

Referring to FIGS. 14-14C, 16-16C, and 17A-17C, the legs 114 of the second extensions 110 can include extended wide flanges 114a that can engage the lamina or sacrum of the corresponding vertebra 84. The flanges 114a can include teeth, serrations or other anti-slip formations 122a, as shown in FIGS. 14A, 16A and 17A, for example. In one aspect, the flanges 114a can include holes for receiving screws or other bone fasteners (not shown). It will be appreciated that the interspinous implant 100 can be used at any level of the spine, including but not limited to the L5-S1 levels.

Figure 15:
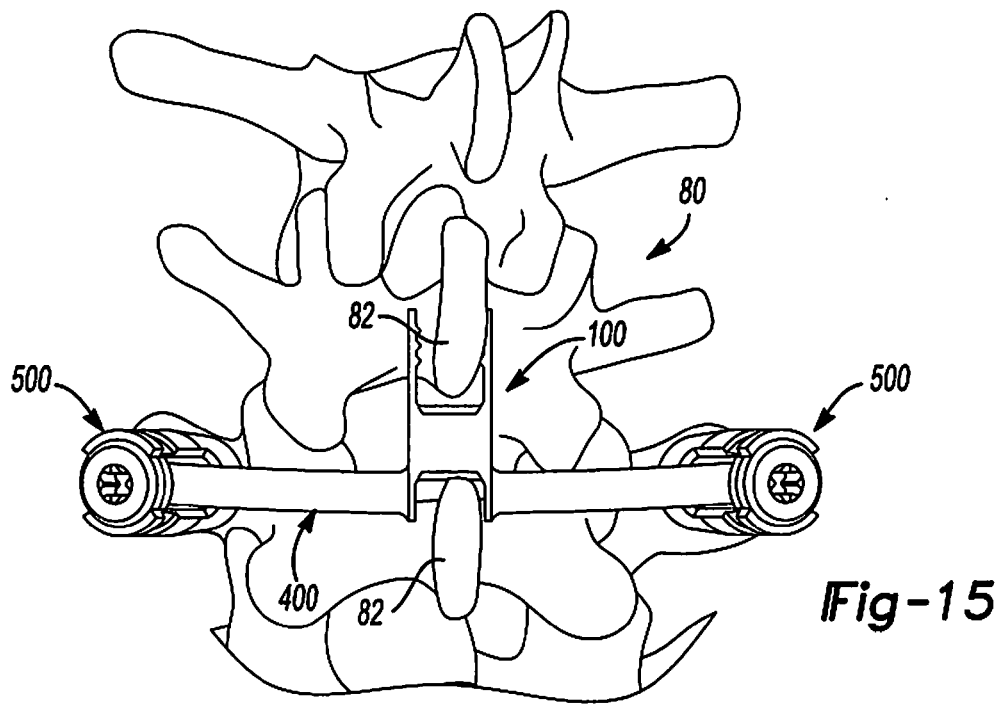
FIG. 15 is an environmental view of an interspinous implant according to the present teachings, the interspinous implant shown implanted in a spine.
Figure 15A:
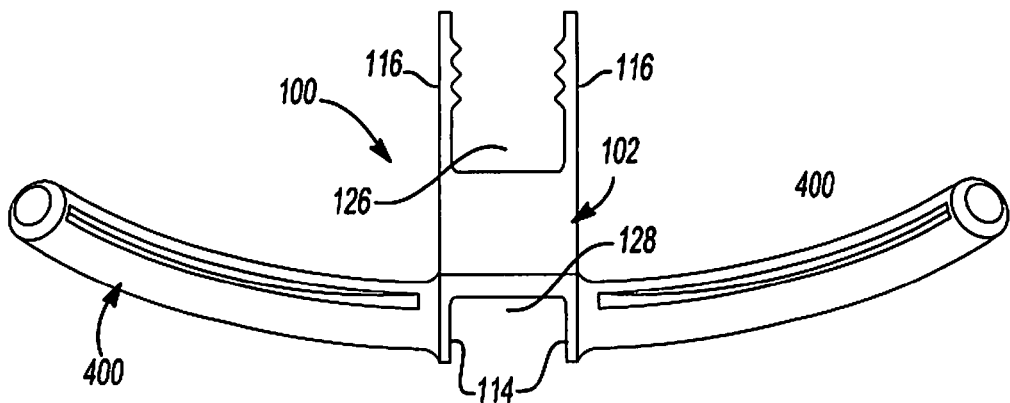
FIG. 15A is a rear view of the interspinous implant of FIG. 15.
Figure 15B:
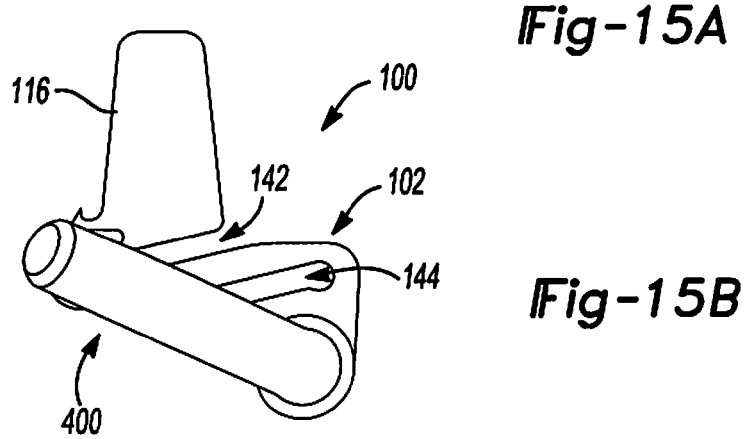
FIG. 15B is a side view of the interspinous implant of FIG. 15.

Referring to FIGS. 15, 15A, and 15B, the interspinous implant 100 can include a spinal connecting element portion 400. The connecting element portion 400 can be formed of a suitable biocompatible metal, metal alloy or polymer, such as titanium or Polyether ether ketone (PEEK). The connecting element portion 400 can extend at an angle outwardly from each of the legs 114 and can be secured to the spine 80 with pedicle screws 500. The connecting element portion 400 can be an integral or modular portion of the interspinous implant 100. The connecting element portion 400 can be curved to follow the anatomy of the spine 80.

Figure 18A:
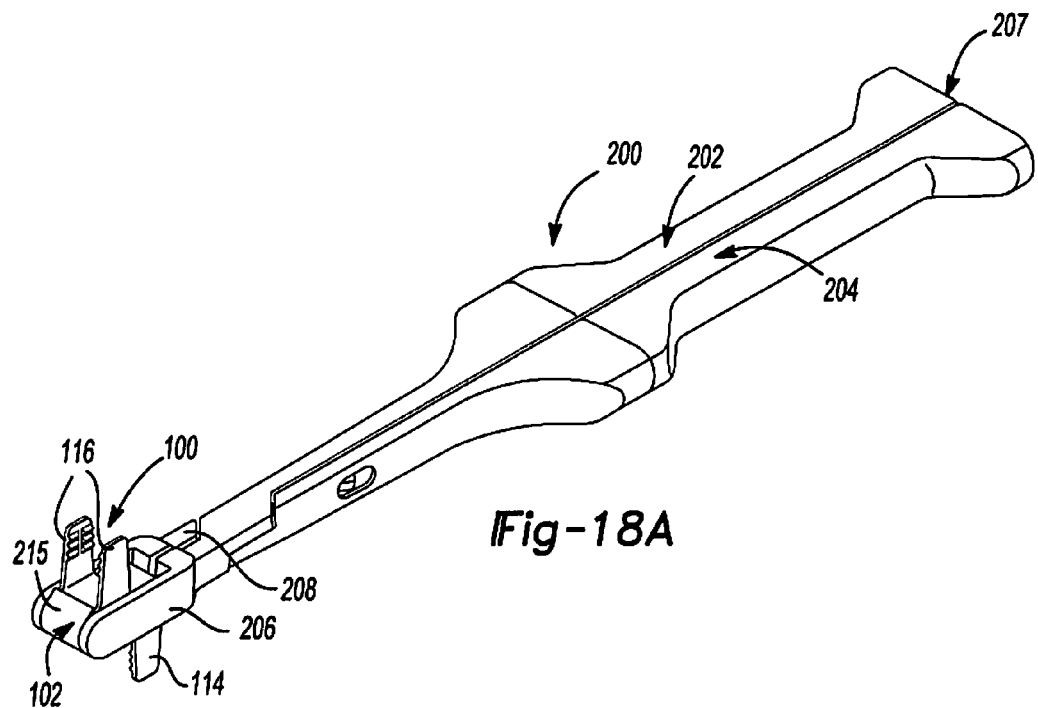
FIG. 18A is a perspective view of an inserter for an interspinous implant according to the present teachings, the inserter shown holding the interspinous implant.
Figure 18B:
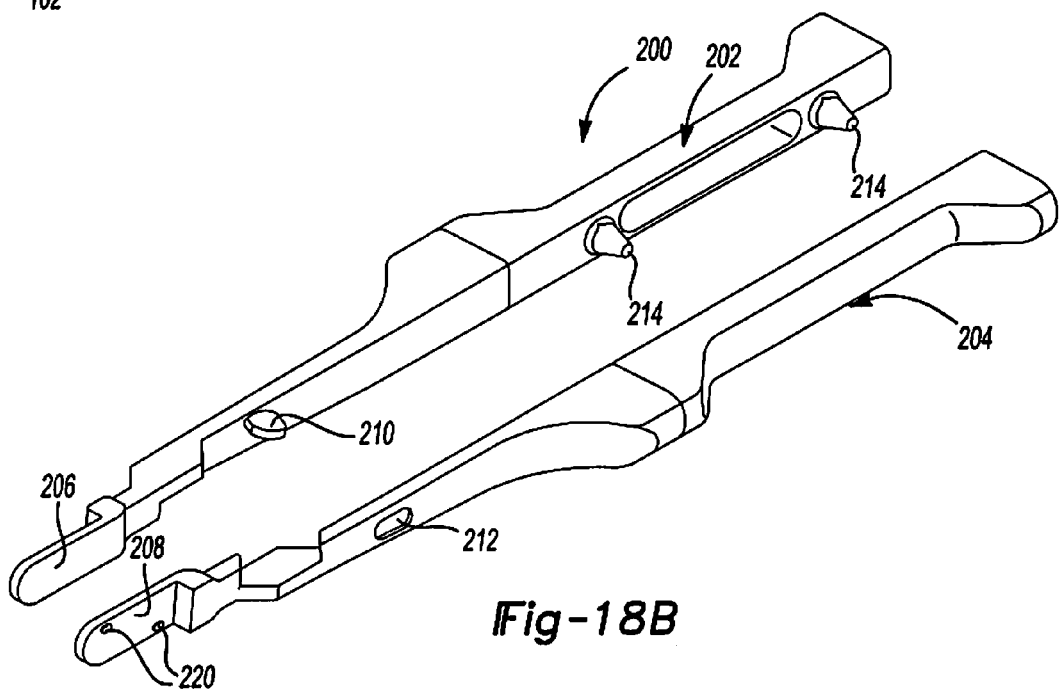
FIG. 18B is an exploded view of the inserter of FIG. 18A.
Figure 19A:
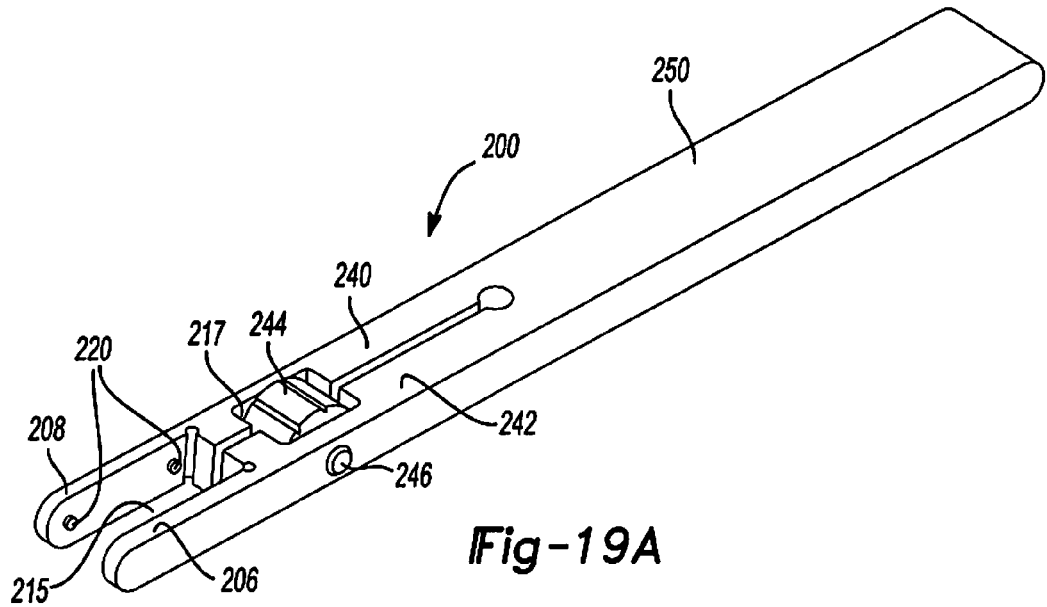
FIG. 19A is a perspective view of an inserter for an interspinous implant according to the present teachings.
Figure 20A:
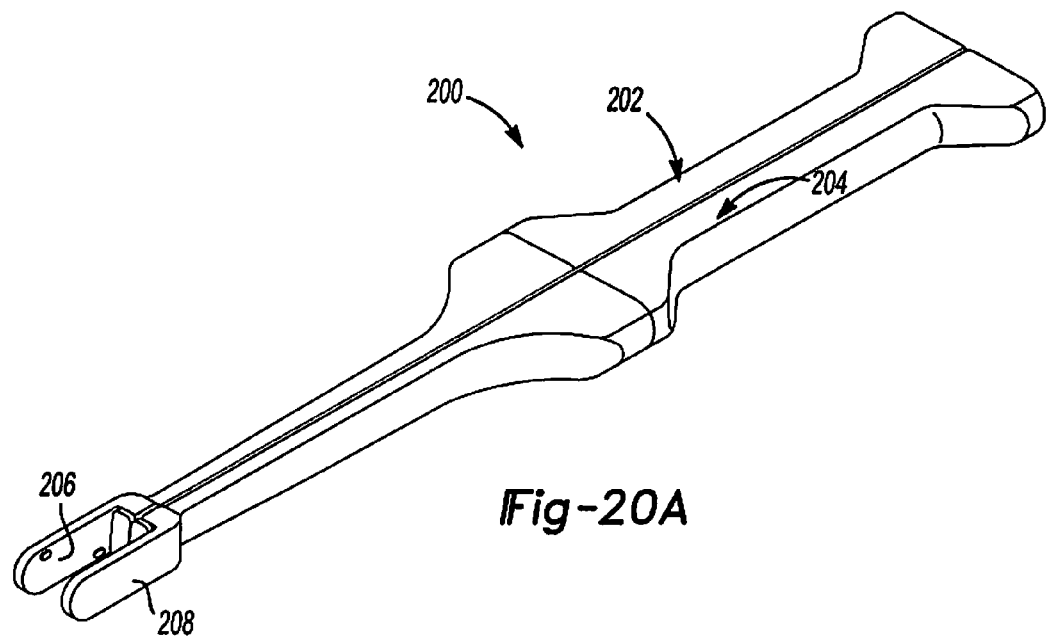
FIG. 20A is a perspective view of an inserter for an interspinous implant according to the present teachings.
Figure 20B:
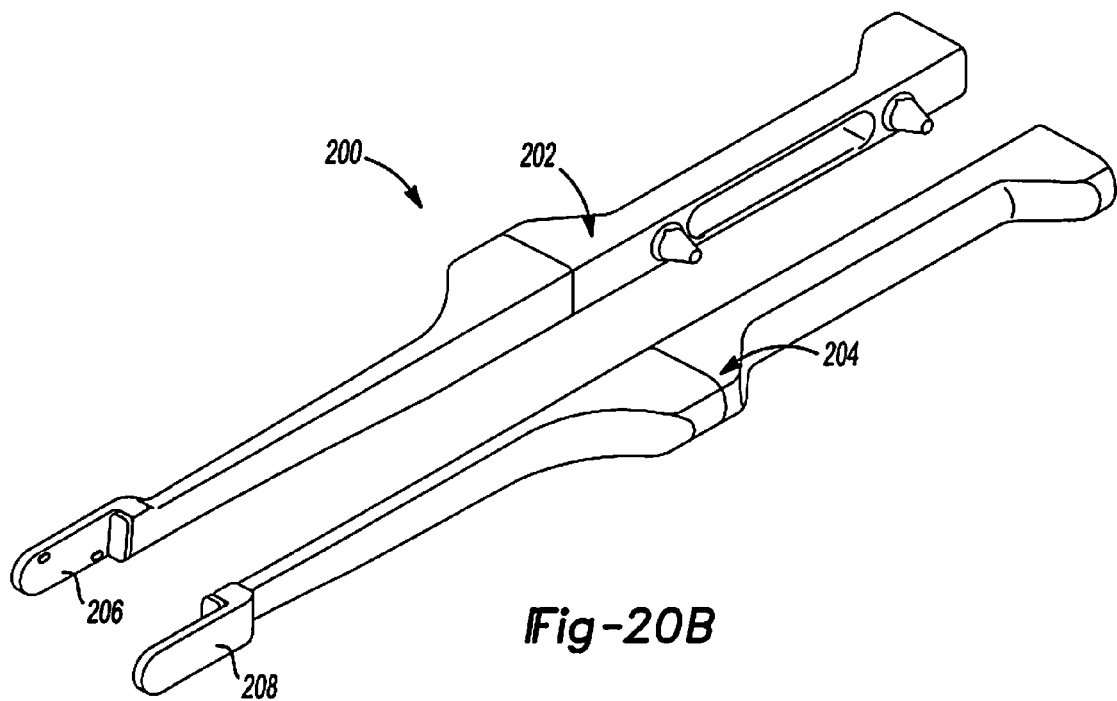
FIG. 20B is an exploded view of the inserter of FIG. 20A.

Referring to FIGS. 4, 13B, 14B, 16B, 17B, the body 102 can also include pairs of superior and inferior recesses 130 for engagement with an insertion/extraction tool 200, referenced as inserter 200 for short. The inserter 200 can be of a scissor-like type, as shown in FIGS. 18A and 18B, or of a tweezer-like type, as shown in FIGS. 19A and 10B, or chop-stick like type, as shown in FIGS. 20A and 20B. The inserter 200 can be made of plastic or metallic materials and can provide cushioning for holding the interspinous implant 100. The inserter 200 can be size specific or universal.

Referring to FIGS. 18A and 18B, the scissor-like inserter 200 can include first and second handles 202, 204 that can be pivotably coupled and include a tongue 210 and an elongated slot 212 that can be engaged to prevent opening. The first and second handles 202, 204 can terminate in crossing and spaced-apart arms 206, 208. Each arm 206, 208 can include a pair of inward-facing protrusions 220 mateable for engagement with the corresponding pairs of recesses 130 of the interspinous implant 100. The spaced-apart arms 206, 208 can define an opening 215 sized to accommodate the size of the interspinous implant 100, as shown in FIG. 18A. The arms 206, 208 can be coated with appropriate materials to provide a better grip, while protecting the interspinous implant 100 from damage. Such materials can include, for example, nylon or polymeric materials that have modulus that is less than the modulus of the interspinous implant 100. At least a portion of the handles 202, 204 can be color coded to visually indicate a particular size of an interspinous implants 100. The handles 202, 204 can include pins or other features 214 for keeping the handles 202, 204 coupled to one another in a closed configuration. The end portions of the handles 202, 204 can define an enlarged surface 207 for attaching a striker plate (not shown) for facilitating insertion of the interspinous implant 100.

Referring to FIGS. 20A and 20B, the chopstick-like inserter 200 is similar to the scissor like inserter 200 shown in FIGS. 18A and 18B, except that the first and second handles 202, 204 are nor pivotably coupled and the arms 206, 208 do not cross each other.

Figure 19B:
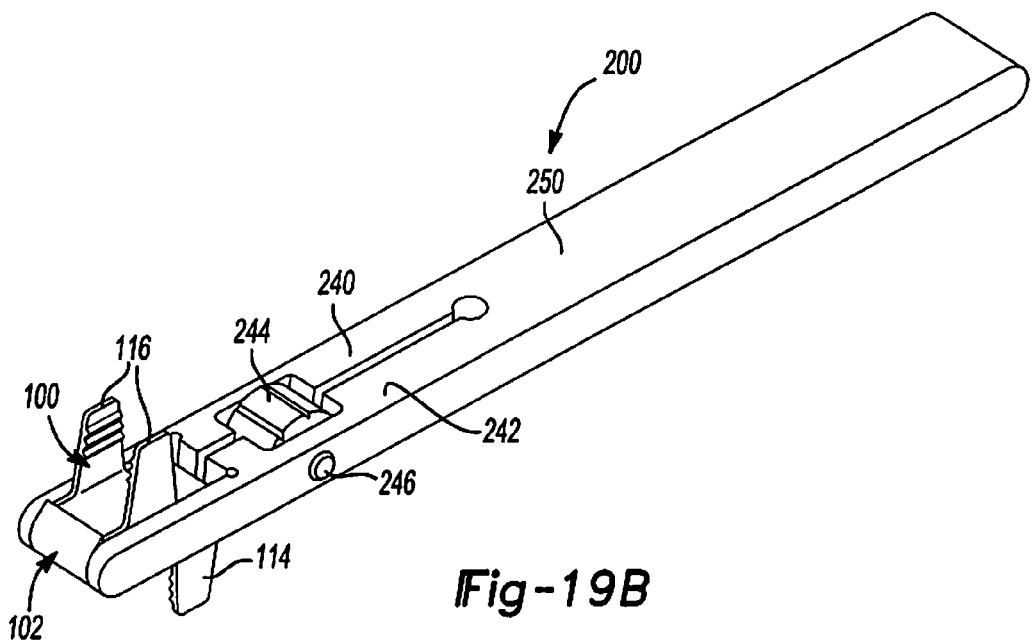
FIG. 19B is a perspective view of the inserter of FIG. 19A, the inserter shown holding the interspinous implant.

Referring to FIGS. 19A and 19B, the tweezer-like inserter 200 can include a handle 250 bifurcating into first and second portions 240, 242 that define an opening for receiving a knob 244 rotatable about a pivot pin 246. The first and second portions 240, 242 can terminate in first and second parallel and spaced apart arms or jaws 208, 206. The arms 206, 208 can define an opening 215 for receiving the interspinous implant 100 and can include inner protrusions 220 for engaging the recesses 130 of the interspinous implant 100. Rotating the knob 244 in opposite directions can urge the arms 208, 206 to move between a first configuration for holding the interspinous implant 100, and a second configuration for releasing the interspinous implant 100. The handle 250 can be sized to operate as a trial sizer by matching certain dimensions of the body 102, such as width and height of the body 102. Optionally, the inserter 200 or a portion thereof can be color-coded to indicate implant size or match similarly color-coded interspinous implants 100.

Figure 21A:
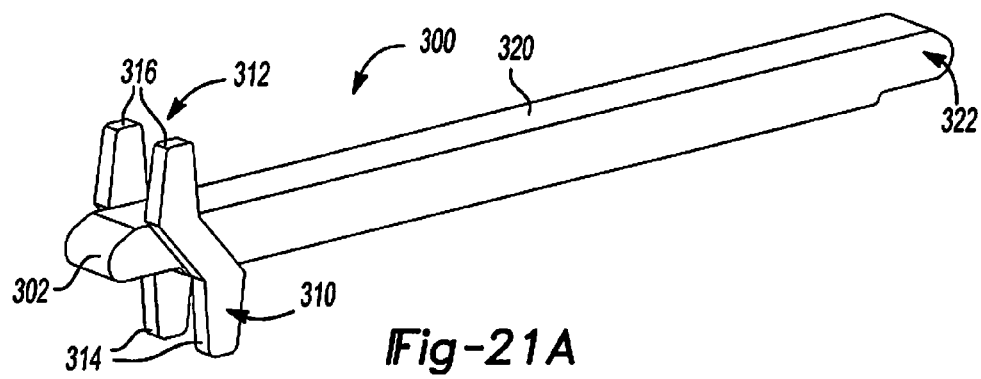
FIG. 21A is a perspective view of a trial sizer for an interspinous implant according to the present teachings.
Figure 21B:
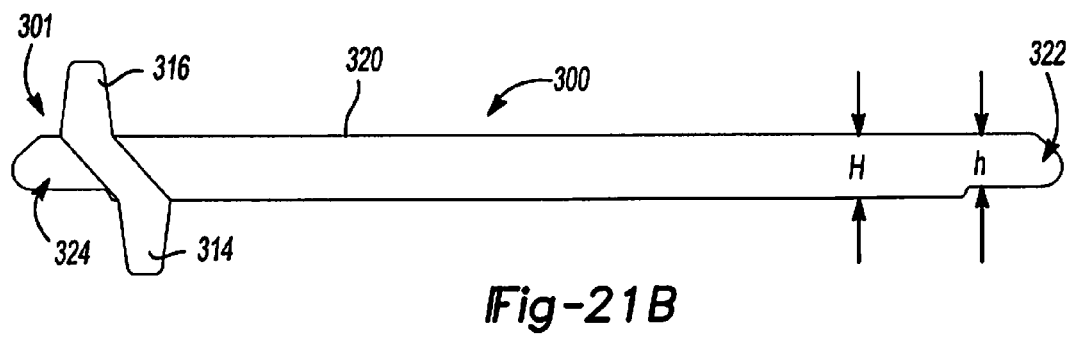
FIG. 21B is a side view of the trial sizer of FIG. 21A.
Figure 21C:
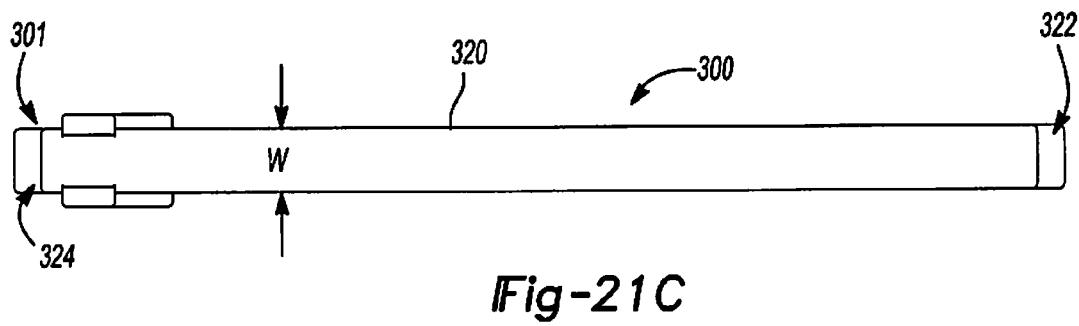
FIG. 21C is a plan view of the trial sizer of FIG. 21A.

Referring to FIGS. 21A-C, a trial sizer 300 can be used in association with the interspinous implant 100. The trial sizer 300 can include a shaft 320 having first and second ends 322, 324. The first end can have a height that matches the height the body 102 of the interspinous implant 100, as discussed below. The second end 324 can have a profile 301 that matches the entire anterior profile of the interspinous implant 100. The profile 301 can include an anterior surface 302 corresponding to the anterior surface of the body 102, and superior and inferior brackets 312, 310 with corresponding pairs of legs 316, 314 that match the profile of the first and second extensions 112, 110 of the interspinous implant 100. Referring to FIGS. 5, 6 and 21A-C, for example, the shaft 320 and the interspinous implant 100 can have matching width "W". Similarly, the heights "H" and "h" of the shaft 320 can match the total height "H" of the body 102 and the height "h" of the U-shaped (saddle) portions 104, 106 of the body.

The interspinous implant 100 can be inserted posteriorly through a minimal skin incision requiring little soft tissue dissection on either of the lateral sides of the spinous process 82 and lamina. The superspinous ligament may be preserved by clipping a small portion of the posterior process bone on the inferior surface of the superior process and the superior surface of the inferior process. A small portion of bone can remain attached to the ligament from both processes. Sufficient bone may be removed such that the ligament can be retracted slightly to one side allow the interspinous implant 100 to be inserted in a direct posterior fashion. After the interspinous implant 100 is inserted, the superspinous ligament can be replaced to fulfill its normal function. The clipped bone fragments (still attached to the ligament) can be reattached via a staple or suture. The bone can then be expected to fuse.

The interspinous implant 100 may also be inserted with complete bisection of the superspinous ligament at the affected level. After the interspinous implant 100 is inserted, the first and second extensions 112, 110 can be crimped down on the processes 82, fixing the interspinous implant 100 to the bone. Because the interspinous implant 100 can be rigidly attached to the superior and inferior spinous processes 82, the tension of the interspinous implant 100 can act as a mechanical replacement of the tension band supplied by the intact ligament. This function of the interspinous implant 100 can facilitate reducing loads in the disc space. The interspinous implant 100 can also be inserted laterally without modifying the spinous processes 82 or the superspinous ligament. The interspinous implant 100 can be inserted through the interspinous space, and then rotated within the sagittal plane into the appropriate position.

Figure 22:
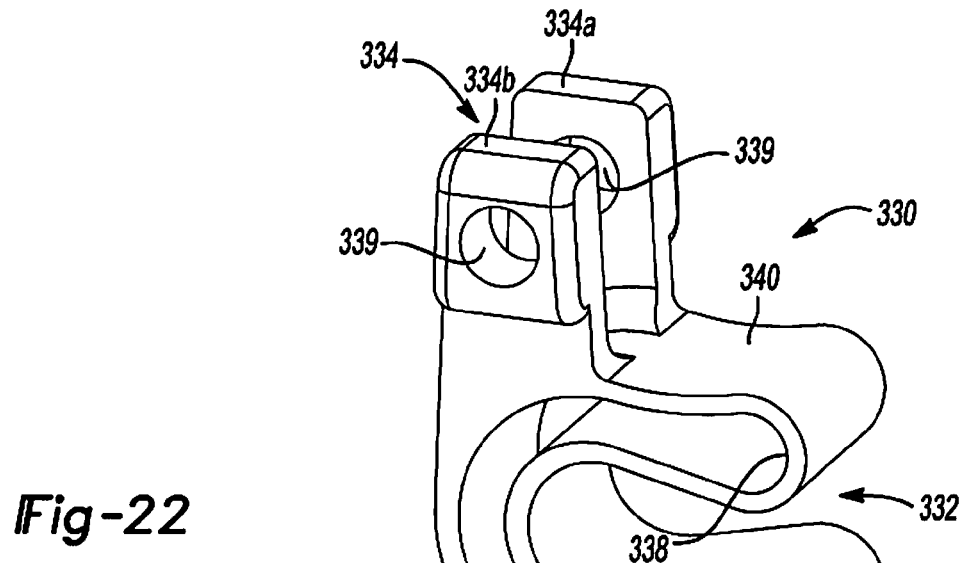
FIG. 22 is a perspective illustration of an exemplary interspinous implant according to various teachings.
Figure 23:
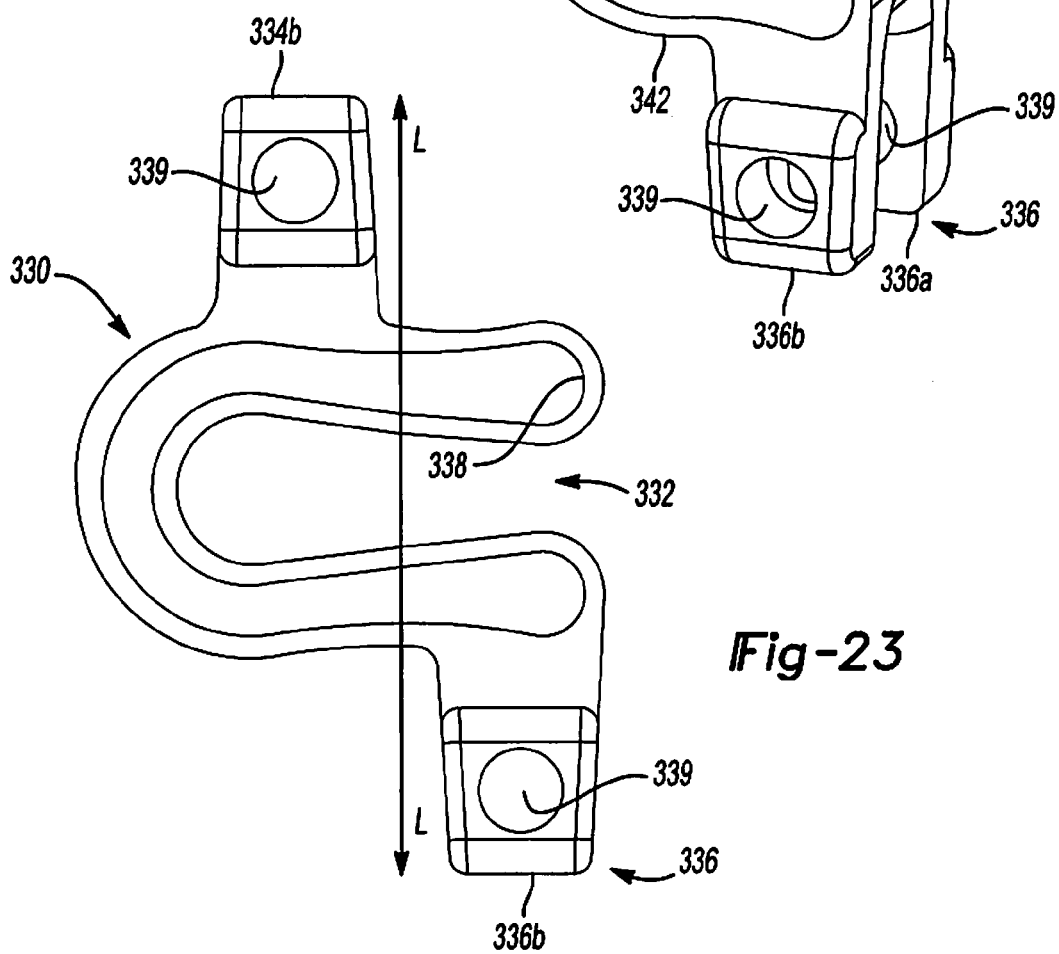
FIG. 23 is a side view of the interspinous implant of FIG. 22.

With reference to FIGS. 22 and 23, another exemplary interspinous implant 330 is shown. As the interspinous implant 330 can be substantially similar to the other interspinous implants 100 described previously herein, the same reference numerals will be used to describe the same or similar items. The interspinous implant 330 can include a body 332, a first extension 334 and a second extension 336. In one example, the body 332, first extension 334 and second extension 336 can be integrally formed out of a suitable biocompatible material, such as a biocompatible metal or polymer, for example, PEEK. The interspinous implant 330 can be implanted between two spinous processes of adjacent vertebrae.

In this example, the body 332 can define a substantially C-shaped aperture 338. The C-shaped aperture 338 can allow the body 332 to reduce loads in the disc space, as previously discussed. The C-shaped aperture 338 can extend through the body 332. In addition, if desired, the C-shaped aperture 338 of the body 332 can be configured such that a portion of the body 332 can extend into the vertebral foramen, as illustrated in FIG. 23. The body 332 can also include a first end 340 opposite a second end 342. The first extension 334 can be coupled to the first end 340, and the second extension 336 can be coupled to the second end 342.

Each of the first extension 334 and the second extension 336 can extend away from the body 332 in a generally U-shape or saddle shape. In this regard, each of the first extension 334 and the second extension 336 can comprise a pair of arms 334a, 334b, 336a, 336b, which can cooperate to form the generally U-shape. Each of the arms 334a, 334b, 336a, 336b can include an aperture 339 for receipt of a suitable fastener to further secure the interspinous implant 330 to the anatomy. The first extension 334 can be generally offset from the second extension 336 relative to a longitudinal axis L of the interspinous implant 330 as best shown in FIG. 23. This can enable the interspinous implant 330 to be used in a multiple level spinal procedure. It should be noted that although the first extension 334 and second extension 336 are illustrated and described herein as being offset form the longitudinal axis L, the first extension 334 and second extension 336 can be positioned as desired relative to the longitudinal axis L.

As the method and use of the interspinous implant 330 can be substantially similar to the method and use of the interspinous spacer 100, for the sake of brevity, the method and use of the interspinous implant 330 need not be discussed herein.

Figures 24, 25:
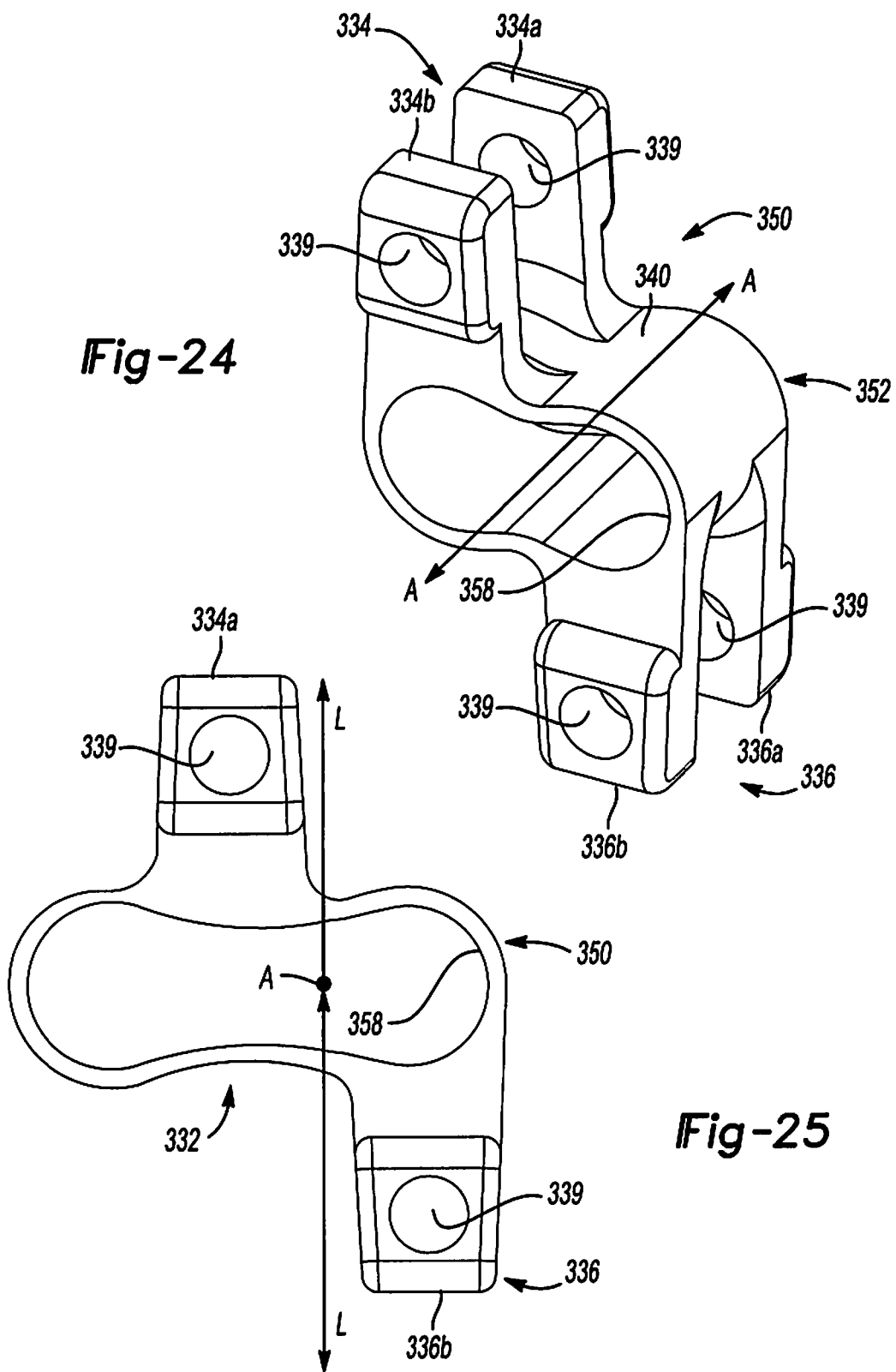
FIG. 24 is a perspective illustration of an exemplary interspinous implant according to various teachings.
FIG. 25 is a side view of the interspinous implant of FIG. 24.

With reference now to FIGS. 24 and 25, another exemplary interspinous implant 350 is shown. As the interspinous implant 350 can be substantially similar to the other interspinous implant 330 described previously herein, the same reference numerals will be used to describe the same or similar items. The interspinous implant 350 can include a body 352, the first extension 334 and the second extension 336. In one example, the body 352, first extension 334 and second extension 336 can be integrally formed out of a suitable biocompatible material, such as a biocompatible metal or polymer, for example, PEEK. The interspinous implant 350 can be implanted between two spinous processes of adjacent vertebrae.

In this example, the body 352 can define a substantially oval-shaped aperture 358. The oval-shaped aperture 358 can allow the body 352 to reduce loads in the disc space, as previously discussed. The oval-shaped aperture 358 can extend through the body 352 along an axis A, which can be traverse or substantially perpendicular to a longitudinal axis of the interspinous implant 350. In addition, if desired, the aperture 358 of the body 352 can be configured such that a portion of the body 352 can extend into the vertebral foramen, as illustrated in FIG. 25. The body 352 can also include the first end 340 opposite the second end 342. The first extension 334 can be coupled to the first end 340, and the second extension 336 can be coupled to the second end 342.

As the method and use of the interspinous implant 350 can be substantially similar to the method and use of the interspinous spacer 100, for the sake of brevity, the method and use of the interspinous implant 350 need not be discussed herein.

Figure 28:
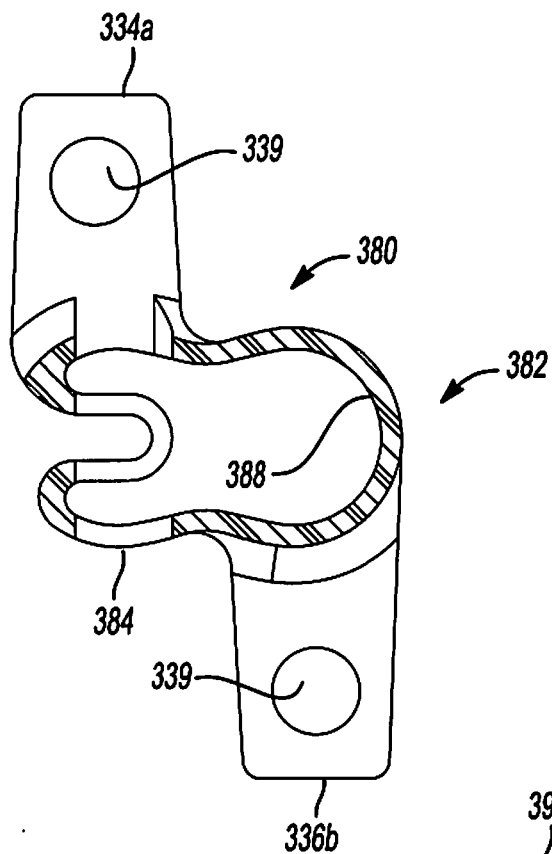
FIG. 28 is a cross-sectional illustration of the interspinous implant of FIG. 26, taken along line 28-28 of FIG. 26.

With reference to FIGS. 26-28, another exemplary interspinous implant 380 is shown. As the interspinous implant 380 can be substantially similar to the other interspinous implant 330 described previously herein, the same reference numerals will be used to describe the same or similar items. The interspinous implant 380 can include a body 382, the first extension 334 and the second extension 336. In one example, the body 382, first extension 334 and second extension 336 can be integrally formed out of a suitable biocompatible material, such as a biocompatible metal or polymer, for example, PEEK. The interspinous implant 380 can be implanted between two spinous processes of adjacent vertebrae.

In this example, the body 382 can define an aperture 388, which can be substantially tooth-shaped. The tooth-shaped aperture 388 can allow the body 382 resiliently deform during loading, as previously discussed. The aperture 388 can extend through the body 382 along an axis A, which can be traverse or substantially perpendicular to a longitudinal axis of the interspinous implant 380. In addition, if desired, the aperture 388 of the body 382 can be configured such that a portion of the body 382 can extend into the vertebral foramen, as illustrated in FIG. 27. The body 382 can also define a bore 384, which can extend through at least a portion of the aperture 388. The bore 384 can receive a secondary fastening device, such as a screw, suture, wire, etc. if desired. Further, if desired, the body 382 could include a slot 385, which can provide the body 382 with additional flexibility. The body 382 can also include the first end 340 opposite the second end 342. As discussed, the first extension 334 can be coupled to the first end 340, and the second extension 336 can be coupled to the second end 342.

As the method and use of the interspinous implant 380 can be substantially similar to the method and use of the interspinous spacer 100, for the sake of brevity, the method and use of the interspinous implant 380 need not be discussed herein.

Figure 29:
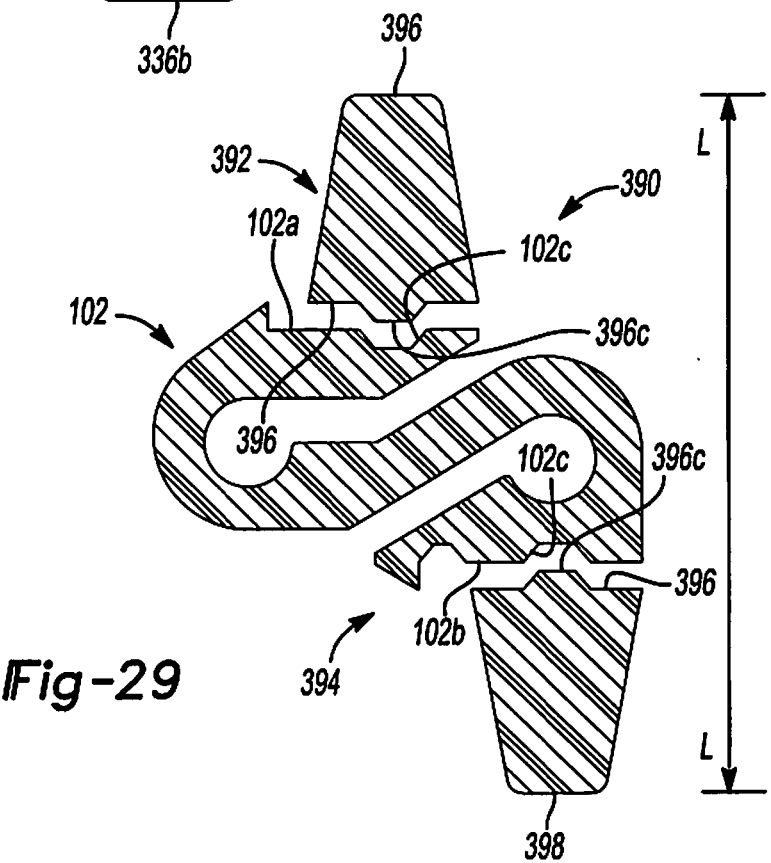
FIG. 29 is a schematic cross-sectional illustration of an exemplary interspinous implant according to various teachings.

With reference to FIG. 29, a cross-sectional view of another exemplary interspinous implant 390 is shown. As the interspinous implant 390 can be substantially similar to the other interspinous implants 100 described previously herein, the same reference numerals will be used to describe the same or similar items. The interspinous implant 390 can be implanted between two spinous processes of adjacent vertebrae. The interspinous implant 390 can include the body 102, a first extension 392 and a second extension 394.

The body 102 can include a first end 102a and a second end 102b. Each of the first end 102a and the second end 102b of the body 102 can include a coupling feature 102c. In one example, the first extension 392 can be modularly or releasably coupled to the first end 102a, via the coupling feature 102c associated with the first end 102a, and the second extension 394 can be modulary or releasably coupled to the second end 102b, via the coupling feature 102c associated with the second end 102b. It should be noted that although both the first extension 392 and the second extension 394 are described and illustrated herein as being discrete components modularly or releasably coupled to the body 102, only one of the first extension 392 or the second extension 394 may be a discrete component, with the other of the first extension 392 and the second extension 394 being integrally formed with the body 102, if desired.

In one example, the first extension 392 and second extension 394 can be formed out of a suitable biocompatible material, such as a biocompatible metal or polymer, for example, PEEK. Further, if desired, the first extension 392 and the second extension 394 can be composed of a different biocompatible material than the body 102. Each of the first extension 392 and the second extension 394 can extend away from the body 102 in a generally U-shape or saddle shape, similar to the first extension 334 and the second extension 336.

In this regard, each of the first extension 392 and the second extension 394 can include a first end 396 and a second end 398. Each first end 396 can include an extension coupling feature 396c, which can cooperate with the coupling feature 102c of the body 102 to couple the first extension 392 and the second extension 394 to a respective one of the first end 102a or second end 102b of the body 102. In one example, the extension coupling feature 396c can comprise a dovetail shaped projection, and the coupling feature 102c can comprise a dovetail shaped groove or slot. In another example, the extension coupling feature 396c can include a taper, and the coupling feature 102c can include a slot having a mating taper. It should be understood, however, that any suitable technique can be used to modularly or releasably couple the first extension 392 and the second extension 394 to the body 102, such as mechanical fasteners, snap-fits, press-fit, etc. In addition, it should be understood that the techniques illustrated herein could be reversed, such that the extension coupling feature 396c can comprise a dovetail shaped groove or slot, while the coupling feature 102c can comprise a dovetail shaped projection, etc.

Generally, the first extension 392 can be coupled to the body 102 so as to be generally offset from the second extension 394 relative to a longitudinal axis L of the interspinous implant 390 as best shown in FIG. 29. It should be noted that although the first extension 392 and second extension 394 are illustrated and described herein as being coupled to the body 102 so as to be offset from the longitudinal axis L, the first extension 392 and second extension 394 can be coupled to the body 102 as desired relative to the longitudinal axis L.

The second end 398 of each of the first extension 392 and the second extension 394 can comprise a pair of arms, which can cooperate to form the generally U-shape or saddle shape. The generally U-shape or saddle shape can receive a corresponding spinous process when the interspinous implant 390 is coupled to the anatomy.

As the method and use of the interspinous implant 390 can be similar to the method and use of the interspinous spacer 100, for the sake of brevity, the method and use of the interspinous implant 390 need not be discussed herein. Briefly, however, once the body 102 is properly positioned within the anatomy through a minimally invasive technique, the first extension 392 can be positioned about a respective spinous process and then coupled to the first end 102a of the body 102. In this regard, the extension coupling feature 396c of the first extension 392 can cooperate with the coupling feature 102c of the body 102 to couple the first extension 392 to the body 102. Likewise, the second extension 394 can be positioned about a respective spinous process and then coupled to the body 102 via the cooperation between the extension coupling feature 396c and the coupling feature 102c of the body 102.

Figure 30:
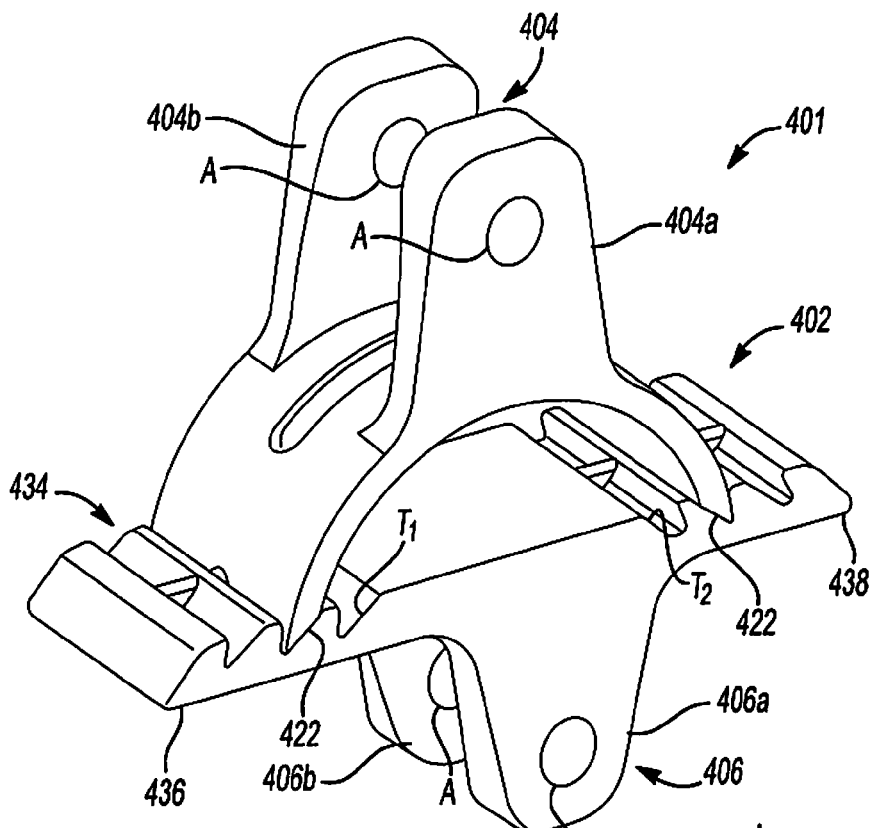
FIG. 30 is a perspective illustration of an exemplary interspinous implant according to various teachings.
Figure 32:
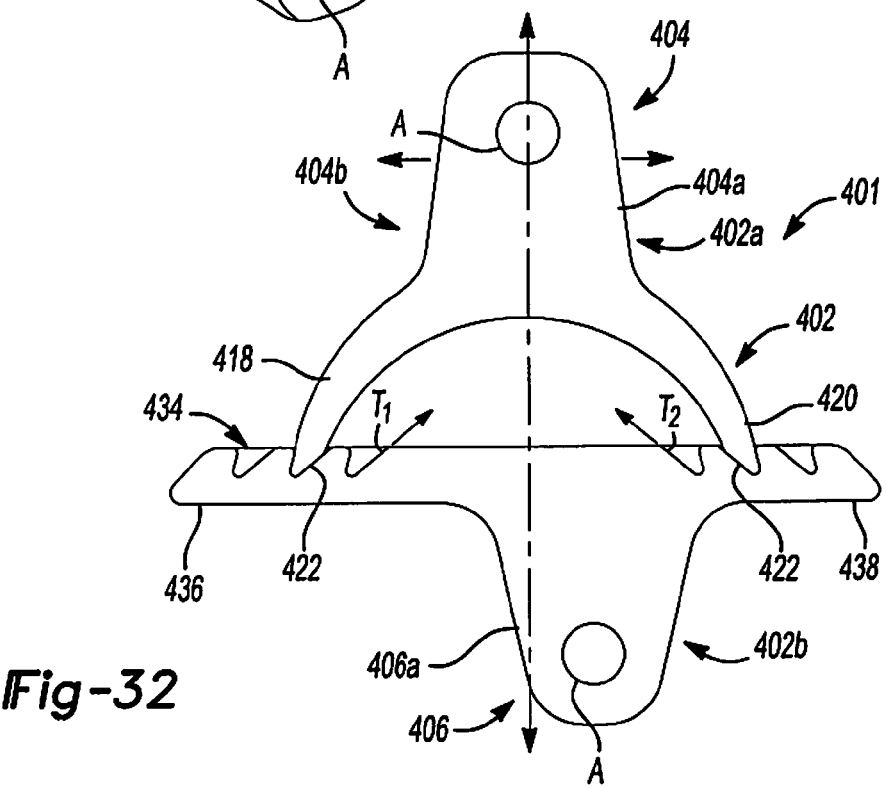
FIG. 32 is a side view of the interspinous implant of FIG. 30.
Figure 31:
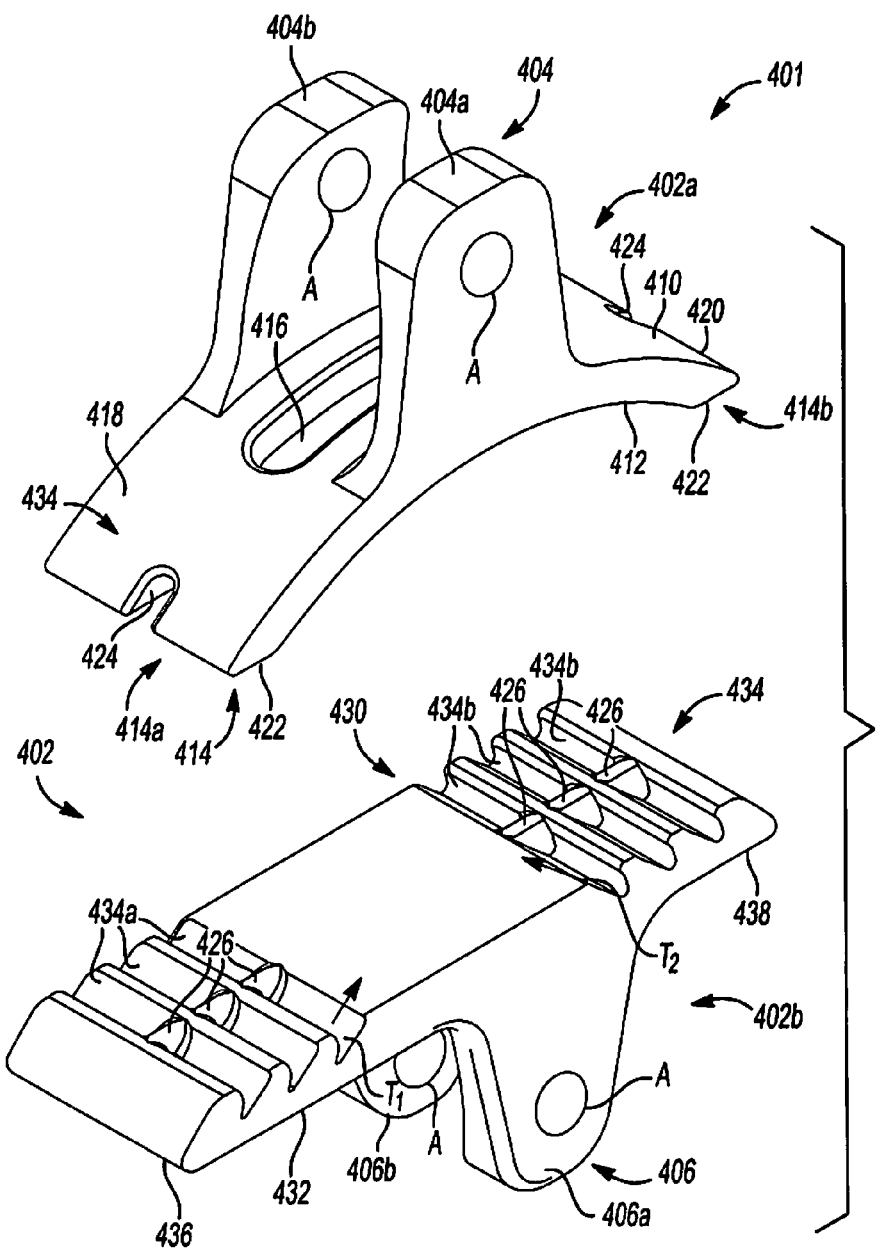
FIG. 31 is an exploded view of the interspinous implant of FIG. 30.

With reference to FIGS. 30-32, another exemplary interspinous implant 401 is shown. As the interspinous implant 401 can be similar to the other interspinous implants 100 described previously herein, the same reference numerals will be used to describe the same or similar items. The interspinous implant 401 can include a body 402, a first extension 404 and a second extension 406. The body 402, first extension 404 and second extension 406 can be formed out of a suitable biocompatible material, such as a biocompatible metal or polymer, for example, PEEK. Generally, the body 402, first extension 404 and second extension 406 can be formed from a suitable biocompatible resilient material. The interspinous implant 401 can be implanted between two spinous processes of adjacent vertebrae.

In one example, the body 402 can comprise a two-piece body assembly, which can include a first member 402a and a second member 402b. The first member 402a and the second member 402b can cooperate to reduce loads within the disc space. The first member 402a can be arcuate or concave in shape. The first member 402a can include a first side 410, a second side 412, at least one mating portion 414 and a slot 416. The first side 410 can be coupled to the first extension 404, while the second side 412 can be adjacent to the second member 402b.

The at least one mating portion 414 can couple the first member 402a to the second member 402b. In this example, with reference to FIG. 31, the at least one mating portion 414 can comprise a first mating portion 414a and a second mating portion 414b. The first mating portion 414a can be disposed at a proximal end 418 of the first member 402a, and the second mating portion 414b can be disposed at a distal end 420 of the first member 402a. Each of the first mating portion 414a and the second mating portion 414b can comprise a rib having a tapered portion 422 and a notch 424. The tapered portion 422 can be configured to engage the second member 402b, as will be discussed. Similarly, the notch 424 can be configured to engage a corresponding projection 426 associated with the second member 402b. Generally, the notch 424 can be formed near or at the middle of the tapered portion 422.

The slot 416 can be formed through the first member 402a, and can extend between the proximal end 418 and the distal end 420. The slot 416 can allow the first extension 404 to move or flex with the anatomy.

The second member 402b can be configured to be coupled to the first member 402a, and can be substantially rectangular in shape. The second member 402b can include a first side 430 opposite a second side 432. The first side 430 can be configured to mate with the first member 402a, while the second extension 406 can be coupled to the second side 432.

The first side 430 can include at least one or a plurality of tapered receiving portions 434. One or more tapered receiving portions 434 can be formed adjacent to each of a proximal end 436 and a distal end 438 of the second member 402b. Generally, tapered receiving portions 434a adjacent to the proximal end 436 can have a taper T1, which can be angled opposite a taper T2 of tapered receiving portions 434b (FIG. 32). The tapered receiving portions 434 can mate with a respective tapered portion 422 of the first mating portion 414a and the second mating portion 414b. In one example, the first side 430 can include three tapered receiving portions 434a adjacent to the proximal end 436 and three tapered receiving portions 434b adjacent to the distal end 438. It should be understood, however, that the first side 430 can include any desired number of tapered receiving portions 434. Further, although the tapered receiving portions 434a are illustrated as being spaced apart from the tapered receiving portions 434b, the tapered receiving portions 434a could be directly adjacent to the tapered receiving portions 434b, if desired. Each of the tapered receiving portions 434 can include the projection 426 to assist in coupling the first member 402a to the second member 402b (FIG. 30). It should be noted, however, that any suitable technique could be used to couple the first member 402a to the second member 402b, and further, that the first mating portion 414a and second mating portion 414b can include additional positive locking features, if desired. In addition, if desired, the tapered receiving portions 434 and the respective tapered portion 422 of the first mating portion 414a can be configured with locking tapers such that the engagement between the tapered receiving portions 434 and the respective tapered portion 422 of the first mating portion 414a can lock the first member 402a to the second member 402b.

In addition, the tapered receiving portions 434 can enable the first member 402a to be coupled to the second member 402b at varying heights. In this regard, depending upon the respective tapered receiving portion 434 the first mating portion 414a and the second mating portion 414b are received within, the first member 402a can be biased into positions of varying heights. This can enable the interspinous implant 401 to be configured to conform to various anatomical geometries. Alternatively, various first members 402a each having a respective height could be selectively employed with the second member 402b to create an interspinous implant 401 with a desired height. Further, the first mating portion 414a and the second mating portion 414b can be coupled to the tapered receiving portions 434 so as to be offset relative to a longitudinal axis L of the interspinous implant 401, which can also allow the interspinous implant 401 to be configured to conform to various anatomical geometries (FIG. 32).

Each of the first extension 404 and the second extension 406 can extend away from the body 402 in a generally U-shape or saddle shape. In this regard, each of the first extension 404 and the second extension 406 can comprise a pair of arms 404a, 404b, 406a, 406b, which can cooperate to form the generally U-shape. Each of the arms 404a, 404b, 406a, 406b can include a radius of curvature, which can aide in securing the interspinous implant 401 to the respective spinous process. In addition, each of the arms 404a, 404b, 406a, 406b can include an aperture A, which can receive a second fastening device, such as a suture, wire, screw, biomechanical fastener, etc. to further couple or secure the body 402 to the anatomy. Further, the arms 404a, 404b, 406a, 406b could include ridges, teeth, scallops, etc. to further grip the spinous processes, if desired.

With the first member 402a coupled to the second member 402b at a desired height, the interspinous implant 401 can be inserted through a minimally invasive surgical procedure, such as the procedures discussed with regard to the interspinous implant 100. Once access to the anatomy has been gained, the first member 402a and the second member 402b can be coupled to the anatomy, such that a respective spinous process is received within each of the first extension 404 and the second extension 406.

Figure 33:
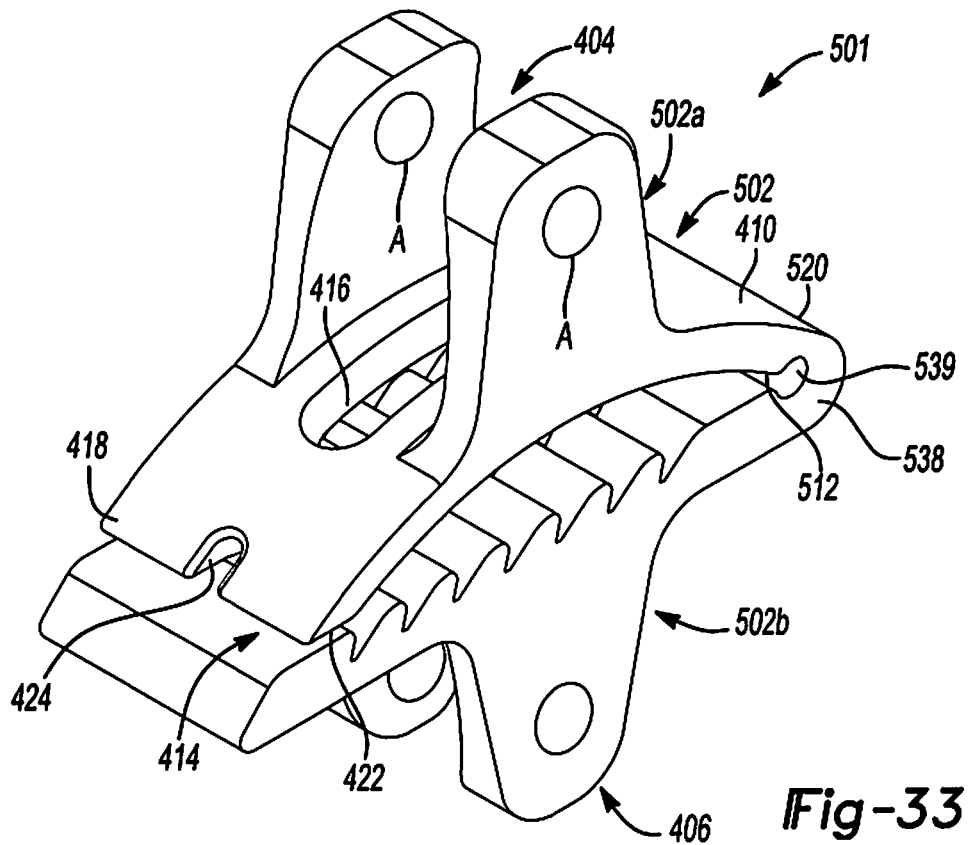
FIG. 33 is a perspective illustration of an exemplary interspinous implant according to various teachings.
Figure 34:
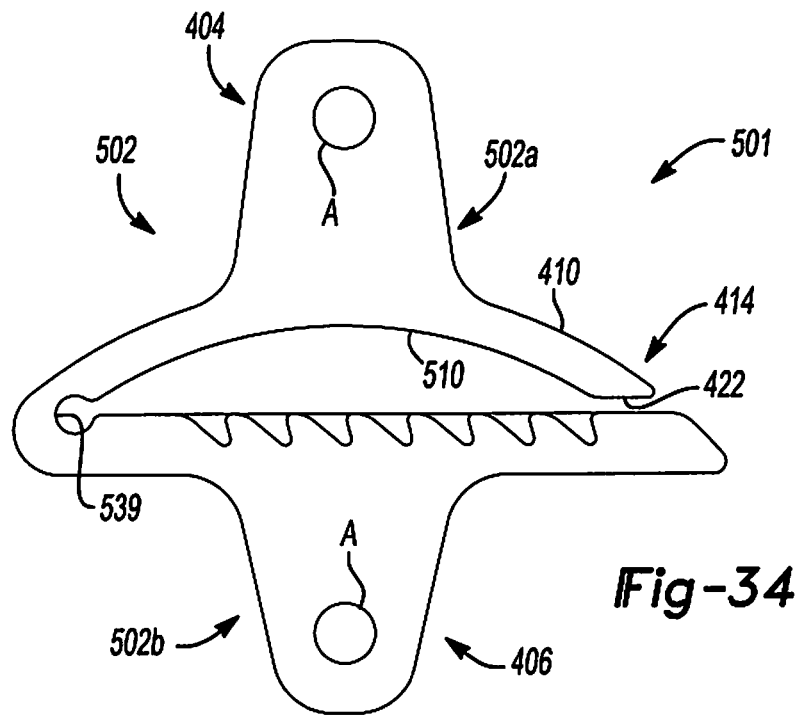
FIG. 34 is a side view of the interspinous implant of FIG. 33.

With reference to FIGS. 33 and 34, an exemplary interspinous implant 501 is shown. As the interspinous implant 501 can be similar to the interspinous implant 401 described with reference to FIGS. 30-32, the same reference numerals will be used to describe the same or similar items. The interspinous implant 501 can include a body 502, the first extension 404 and the second extension 406. The body 502, first extension 404 and second extension 406 can be formed out of a suitable biocompatible material, such as a biocompatible metal or polymer, for example, PEEK. Generally, the interspinous implant 501 can be formed from a resilient biocompatible material, however, the interspinous implant 501 could also be bent into a desired shape using a suitable device. The interspinous implant 501 can be implanted between two spinous processes of adjacent vertebrae.

In this example, the body 502 can comprise a one-piece body assembly, which can include a first member 502a coupled to a second member 502b. The first member 502a can be arcuate or concave in shape. The first member 502a can include the first side 410, a second side 512, the at least one mating portion 414 and the slot 416. The first side 410 can be coupled to the first extension 404, while the second side 412 can be coupled to the second member 502b.

In this regard, the first member 502a can include the proximal end 418 and a distal end 520. The distal end 520 can be coupled to a distal end 538 of the second member 502b. In this example, the first member 502a can be integrally formed with the second member 502b and connected together at the distal ends 520, 538. It should be noted, however, that that first member 502a can be coupled to the second member 502b via any suitable technique, such as mechanical fasteners, or secondary processing techniques. Generally, the first member 502a can be coupled to the second member 502b so as to form a living hinge 539. This can allow the first member 502a to engage the second member 502b at varying heights and orientations. In addition, if desired, the interspinous implant 501 can be configured such that a portion of the first member 502a and the second member 502b can extend into the vertebral foramen.

In this example, the at least one mating portion 414 can comprise the first mating portion 414a, which can engage the tapered receiving portions 434a of the second member 502b. Depending upon which tapered receiving portion 434a coupled to the first mating portion 414a, the height of the interspinous implant 501 can vary, along with the angular orientation of the first extension 404 relative to a longitudinal axis L of the implant 501. This can allow the interspinous implant 501 to be used in various anatomical structures.

The second member 502b can be configured to be coupled to the first member 502a, and can include a first side 530 opposite the second side 432. The first side 530 can include one or more tapered receiving portions 434a, which can extend along the first side 530 between the proximal end 436 and the distal end 538. In one example, the first side 530 can include seven ribs having tapered receiving portions 434a between the proximal end 436 and the distal end 538. It should be understood, however, that the first side 530 can include any desired number of tapered receiving portions 434.

As the method and use of the interspinous implant 501 can be substantially similar to the method and use of the interspinous implant 401, for the sake of brevity, the method and use of the interspinous implant 501 need not be discussed herein.

Figure 35:
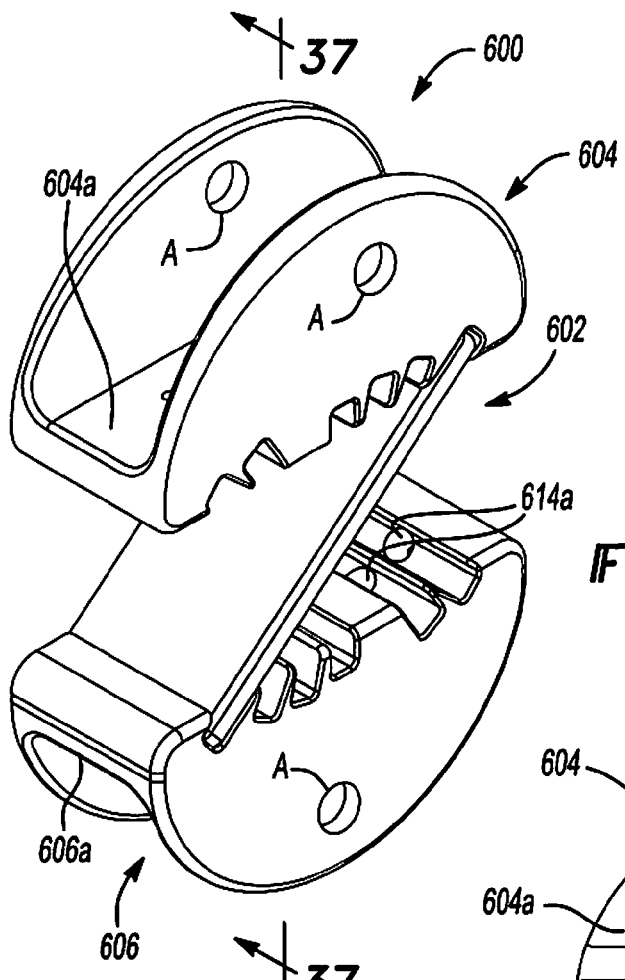
FIG. 35 is a perspective illustration of an exemplary interspinous implant according to various teachings.
Figure 37:
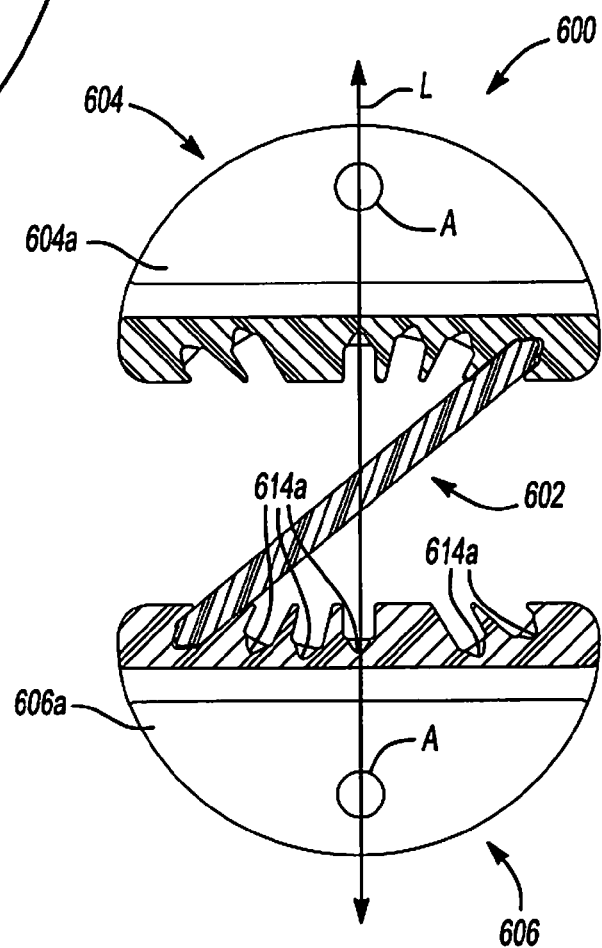
FIG. 37 is a cross-sectional illustration of the interspinous implant of FIG. 35, taken along line 37-37 of FIG. 35.
Figure 36:
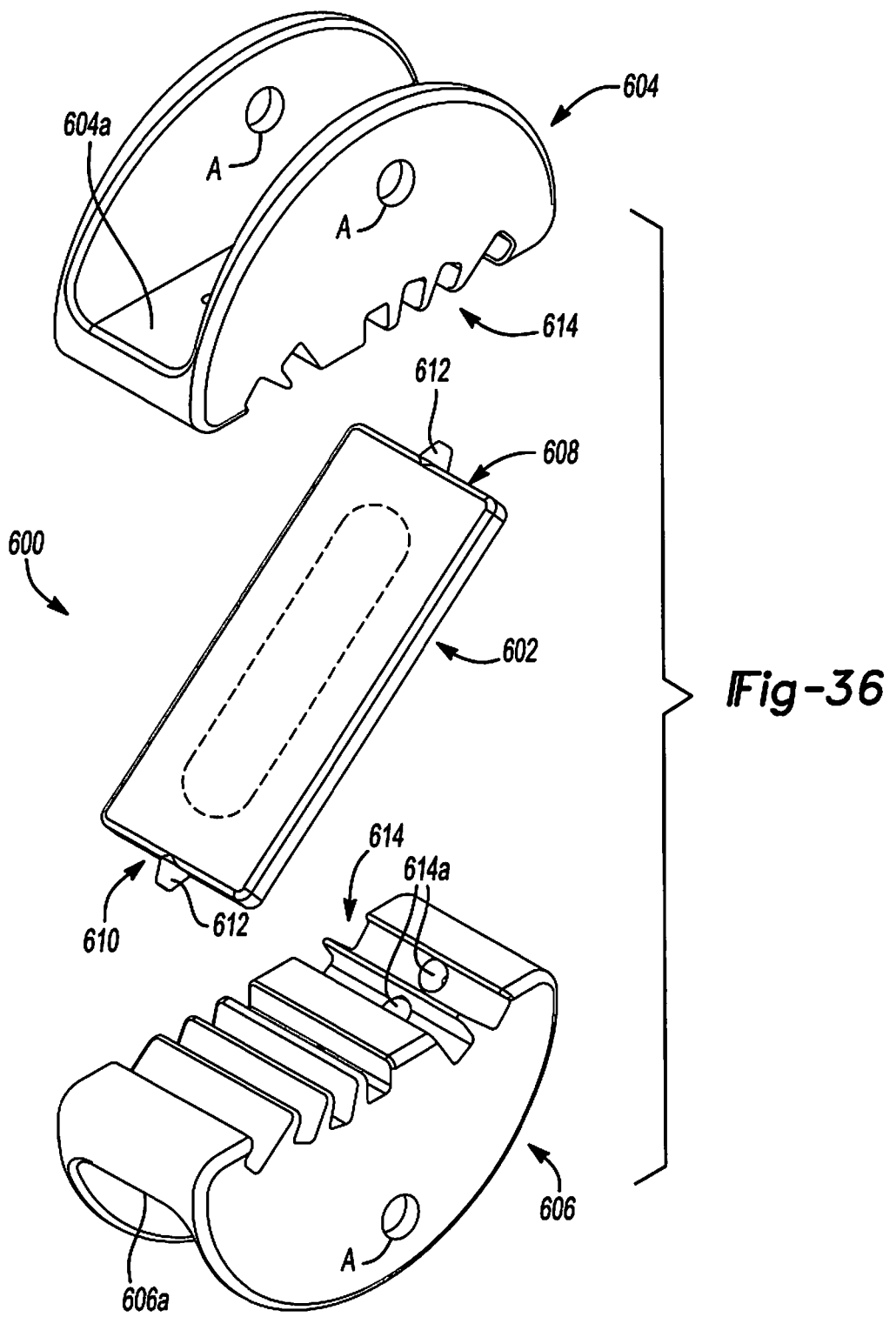
FIG. 36 is an exploded view of the interspinous implant of FIG. 35.

With reference to FIGS. 35-37, another exemplary interspinous implant 600 is shown. As the interspinous implant 600 can be similar to the interspinous implants 100, 401 described previously herein, the same reference numerals will be used to describe the same or similar items. The interspinous implant 600 can include a body 602, a first extension 604 and a second extension 606. The body 602, first extension 604 and second extension 606 can each be formed out of a suitable biocompatible material, such as a biocompatible metal or polymer, for example, PEEK. The interspinous implant 600 can be implanted between two spinous processes of adjacent vertebrae at a desired height.

In one example, the body 602 can comprise a rectangular member, which can couple the first extension 604 to the second extension 606. It should be noted that although a single body 602 is illustrated herein, any number of bodies 602 could be employed to couple the first extension 604 to the second extension 606, and if multiple bodies 602 are employed, they can each include notches or slots so as to enable the bodies 602 to be assembled together between the first extension 604 and the second extension 606. The body 602 can include a first end 608 and a second end 610. Optionally, the body 602 can include a slot, which can provide the body with additional flexibility.

Each of the first end 608 and the second end 610 can include a mating portion or projection 612, which can cooperate with a portion of the first extension 604 and second extension 606 to couple the body 602 to each of the first extension 604 and second extension 606. Although the projection 612 is illustrated herein as being substantially conical, the projection 612 can have any suitable shape, such as spherical, cylindrical, rectangular, etc. In addition, it should be noted that the projection 612 can be optional, as the first end 608 and the second end 610 alone may be suitable to couple the body 602 to the first extension 604 and the second extension 606. The first extension 604 can be coupled to the first end 608 of the body 602, while the second extension 606 can be coupled to the second end 610 of the body 602.

In this regard, each of the first extension 604 and the second extension 606 can include one or more slots 614, which can receive a respective one of the first end 608 and the second end 610 of the body 602. Generally, a majority of the slots 614 can be defined at an angle relative to a longitudinal axis L of the interspinous implant 600, and in one example, the slots 614 of the first extension 604 can be defined as a mirror image of the slots 614 of the second extension 606 (FIG. 37). Thus, when assembled, in one example, the body 602 can extend along a plane transverse to the longitudinal axis L, and can be coupled to the slots 614 so as to vary the height of the interspinous implant 600.

Further, at least one of the slots 614 of each of the first extension 604 and second extension 606 can be formed about the longitudinal axis L such that when assembled, the body 602 extends parallel to the longitudinal axis L, such that the interspinous implant 600 is at a maximum height. It should be understood, however, that although each of the first extension 604 and second extension 606 are illustrated herein as including six angled slots 614, the first extension 604 and second extension 606 can have any number of slots 614, which may or may not be angled relative to the longitudinal axis L. Each of the slots 614 can include a bore 614a, which can be configured to receive the projection 612 associated with each of the first end 608 and second end 610 of the body 602. In addition, if desired, each of the bores 614a can include a taper, which can cooperate with the projection 612 to lock the body 602 to the first extension 604 and the second extension 606.

The first extension 604 and second extension 606 can also each define a generally U-shape or saddle shape for receipt of a respective spinous process. In this regard, each of the first extension 604 and the second extension 606 can define a channel 604a, 606a, which can be formed generally opposite the slots 614. The channel 604a, 606a, can be sized to receive the respective spinous process, and if desired, can include additional features to aid in securing the interspinous implant 600 to the anatomy. In addition, each of the first extension 604 and the second extension 606 can include the aperture A, which can receive a second fastening device, such as a suture, wire, screw, biomechanical fastener, etc. to further couple or secure the first extension 604 and the second extension 606 to the anatomy.

As the method and use of the interspinous implant 600 can be substantially similar to the method and use of the interspinous implant 501, for the sake of brevity, the method and use of the interspinous implant 600 need not be discussed herein. Briefly, however, the interspinous implant 600 can be inserted between the spinous processes through a minimally invasive procedure, such as those described previously herein. In one example, the first extension 604 and second extension 606 can be coupled to the anatomy, and then the first end 608 of the body 602 can be inserted into a respective slot 614 of the first extension 604, and the second end 610 can be inserted into a corresponding slot 614 of the second extension 606 so that the interspinous implant 600 is at a desired height.

Figure 38:
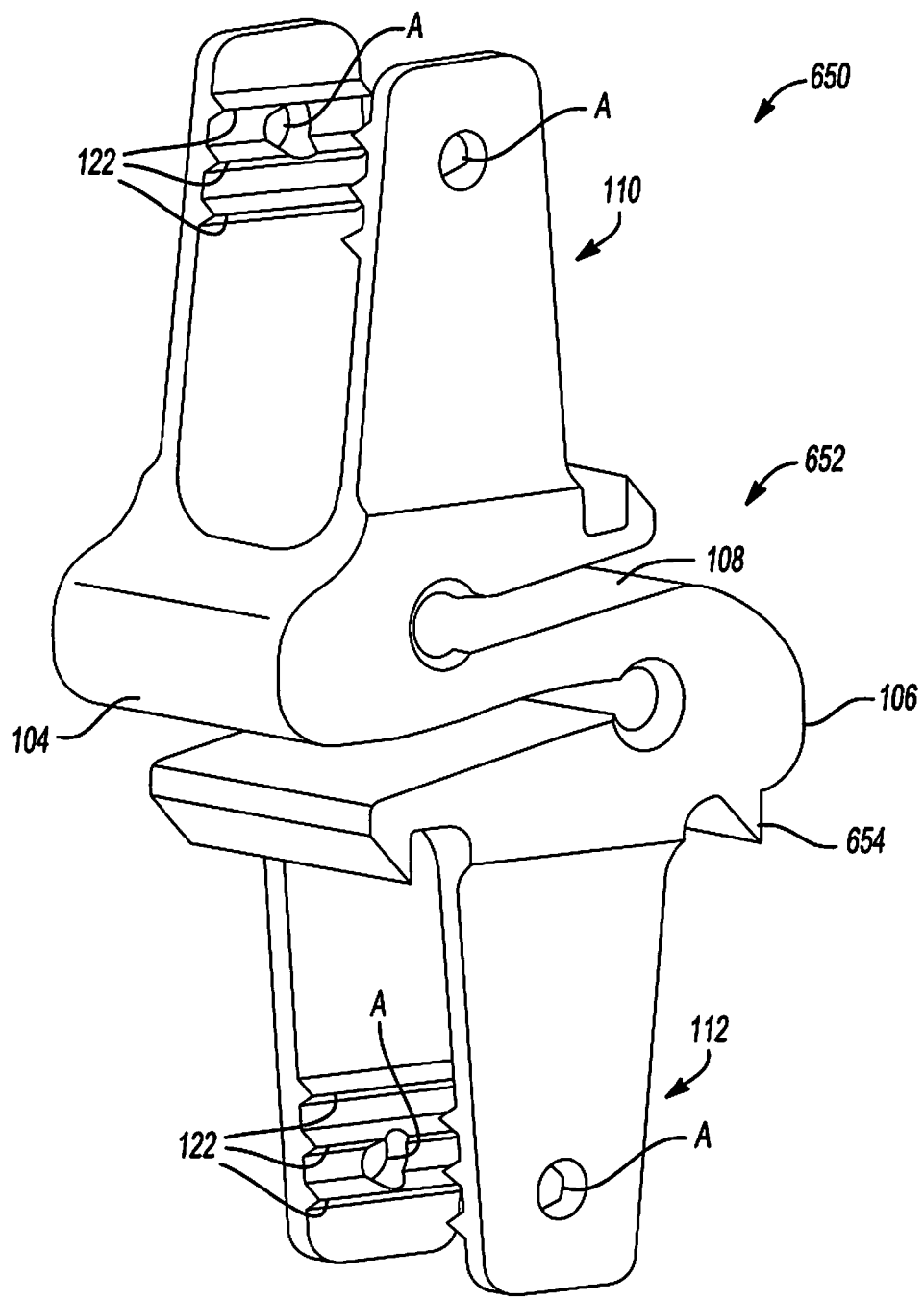
FIG. 38 is a perspective illustration of an exemplary interspinous implant according to various teachings.
Figure 40:
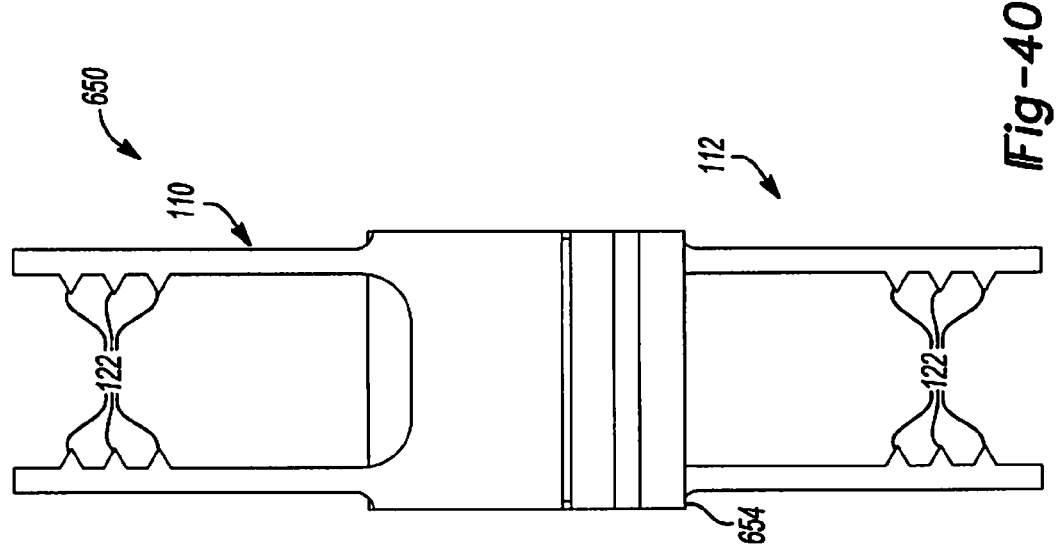
FIG. 40 is a front view of the interspinous implant of FIG. 38.
Figure 39:
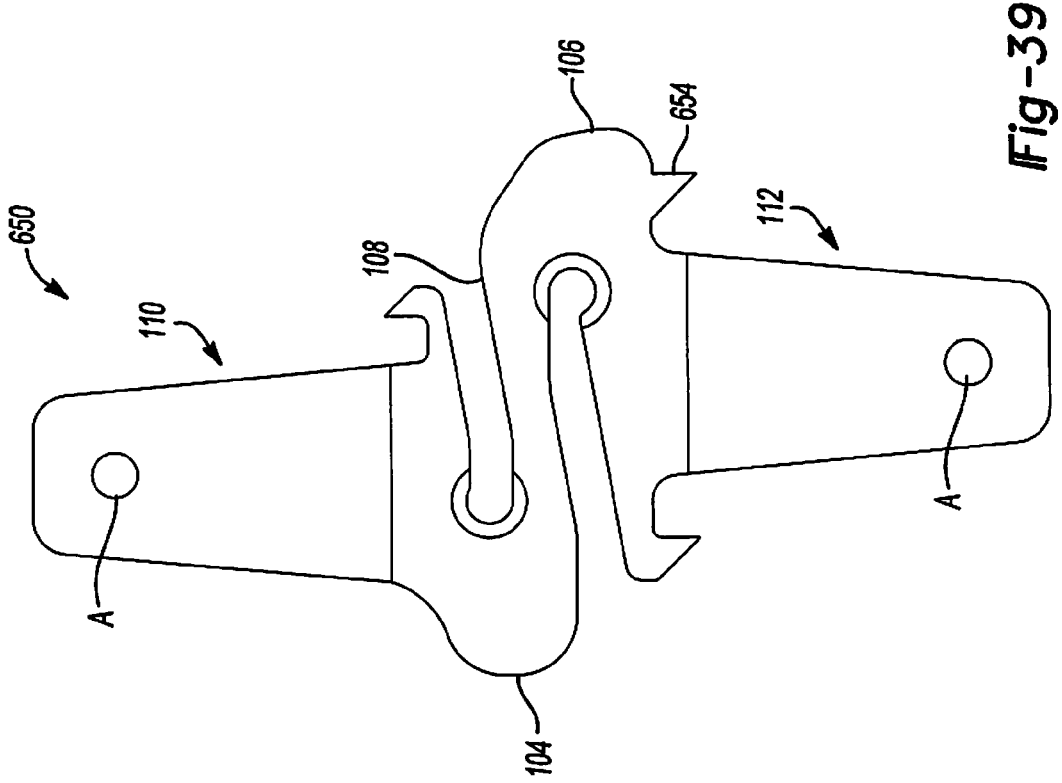
FIG. 39 is a side view of the interspinous implant of FIG. 38.

With reference to FIGS. 38-40, another exemplary interspinous implant 650 is shown. As the interspinous implant 650 can be substantially similar to the other interspinous implants 100 described previously herein, the same reference numerals will be used to describe the same or similar items. The interspinous implant 650 can include a body 652, the first extension 110 and the second extension 112. In one example, the body 652, first extension 110 and second extension 112 can be integrally formed out of a suitable biocompatible material, such as a biocompatible metal or polymer, for example, PEEK. The interspinous implant 650 can be implanted between two spinous processes of adjacent vertebrae. In this example, the first extension 110 and the second extension 112 can each include an aperture A, which can enable receipt of a secondary fastening mechanism, such as a suture, mechanical fastener, etc., to further couple the interspinous implant 650 to the anatomy. Further, the first extension 110 and the second extension 112 may include anti-slip formations 122, with or without the coronal break 124.

The body 652 can include the first U-shaped portion 104, the second U-shaped portion 106 and the intermediate portion 108. The body 652 can also include an angled projection 654, which can be formed adjacent to the second U-shaped portion 106. The angled projection 654 can alter or bite into a portion of the adjacent spinous process to further couple or secure the interspinous implant 650 to the anatomy.

As the method and use of the interspinous implant 650 can be substantially similar to the method and use of the interspinous spacer 100, for the sake of brevity, the method and use of the interspinous implant 650 need not be discussed herein.

With reference to FIGS. 41-43, another exemplary interspinous implant 660 is shown. As the interspinous implant 660 can be substantially similar to the other interspinous implants 100 described previously herein, the same reference numerals will be used to describe the same or similar items. The interspinous implant 660 can include a body 662, a first endplate 664 and a second endplate 668. In one example, the body 662, first endplate 664 and second endplate 668 can be integrally formed out of a suitable biocompatible material, such as a biocompatible metal or polymer, for example, PEEK. It should be noted, however, that one or more of the body 662, first endplate 664 and second endplate 668 could comprise a discrete component, which could be coupled to the other components through suitable manufacturing techniques to form the interspinous implant 600. The interspinous implant 660 can be implanted between two spinous processes of adjacent vertebrae.

In this example, the body 662 can be annular, and can include a first ramped portion 662a opposite a second ramped portion 662b (FIG. 43), and a first end 670 opposite a second end 672 (FIG. 42). The first ramped portion 662a and second ramped portion 662b can be spaced apart by opposite planar portions 669. The planar portions 669 can be in contact with a respective one of the adjacent spinous processes in a first, insertion position, while the first ramped portion 662a and second ramped portion 662b can contact a respective one of the adjacent spinous processes in a second, distraction position. Thus, the first ramped portion 662a and second ramped portion 662b can be cooperate to enable the distraction of the adjacent spinous processes by the rotation of the body 662 within a space defined between the adjacent spinous processes.

In this regard, as shown in FIG. 43, the body 662 can define a first height H1 for insertion and a second height H2 for distraction. The first height H1 can be less than the second height H2. Thus, when rotated about the first ramped portion 662a and second ramped portion 662b from a first, insertion position to a second, distraction position, the body 652 can enable distraction of the adjacent spinous processes. In addition, it should be noted that the first ramped portion 662a and second ramped portion 662b can include one or more teeth to enable the first ramped portion 662a and second ramped portion 662b to bite into the respective spinous process after distraction.

The first end 670 of the body 652 can be coupled to the first endplate 664 and the second end 672 can be coupled to the second endplate 668. The first endplate 664 and the second endplate 668 can be annular, and can cooperate to define a first extension 674 and a second extension 676, as shown in FIG. 42. The first extension 674 and the second extension 676 can receive a respective spinous process when the interspinous implant 660 is coupled to the anatomy. It should be noted that although the first endplate 664 and the second endplate 668 are described and illustrated herein as being annular in shape, the first endplate 664 and the second endplate 668 can have any desired shape suitable for receipt of the adjacent spinous processes therein. The first endplate 664 and the second endplate 668 can be generally integrally formed with the body 662, however, the first endplate 664 and the second endplate 668 could be discrete components coupled to the body 662 through a suitable technique, such as biocompatible fasteners, adhesive, welding, etc.

As the method and use of the interspinous implant 660 can be substantially similar to the method and use of the interspinous spacer 100, for the sake of brevity, the method and use of the interspinous implant 660 need not be discussed herein. Briefly, however, the interspinous implant 660 can be inserted through a minimally invasive technique such that the body 652 is in the first, insertion position and the planar portions 669 can be in contact with the adjacent spinous processes. Then, using the first ramped portion 662 and second ramped portion 662b, the body 652 can be rotated into the second, distracted position to adjust the spinous processes to the second height H2.

As discussed, the interspinous implants 330, 350, 380, 390, 650 can be resilient and act as a tension spring to reduce loads in the disc space. Further, the interspinous implants 401, 501, 600, 660 can be adjusted to varying heights, which can enable the interspinous implants 401, 501, 600, 660 to be employed with various different anatomical structures. Further, each of the interspinous implants 330, 350, 380, 390, 401, 501, 600, 650, 660 can be inserted via a minimally invasive procedure, which can reduce surgical recovery times.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

Figures 44, 45:
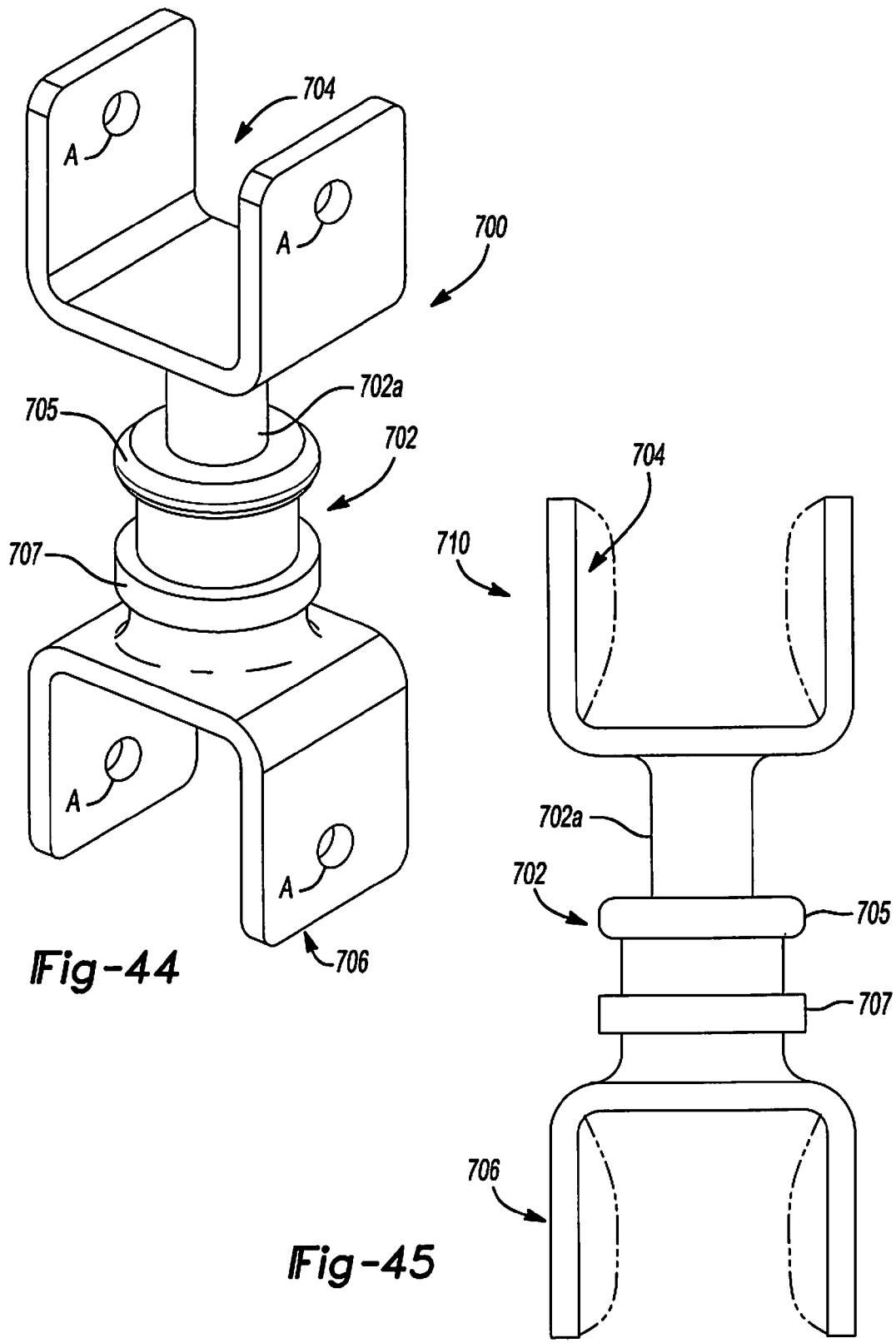
FIG. 44 is a perspective illustration of an exemplary interspinous implant according to various teachings.
FIG. 45 is a side view of the interspinous implant of FIG. 44.

For example, while the interspinous implant 100 has been described herein as having an S-shaped body that allows the interspinous implant 100 to act as a tension spring, those of skill in the art will appreciate that the present disclosure, in its broadest aspects, may be constructed somewhat differently. In this regard, with reference to FIGS. 44 and 45, an interspinous implant 700 can include a body 702, a first extension 704 and a second extension 706. In this example, the body 702 can include a telescoping shaft 702a, which can allow the interspinous implant 700 to resiliently deform under loads applied by the adjacent spinous processes. In this regard, the first extension 704 and the second extension 706 can each receive a respective spinous process. The first extension 704 and the second extension 706 can have any desired shape to couple the first extension 704 and the second extension 706 to the adjacent spinous processes, such as arcuate. Under the application of loads from either spinous process, such as during flexion or extension, the telescoping shaft 702a can move or slide, which can reduce loading in the disc space.

In addition, if desired, the interspinous implant 700 can include a locking ring 705 and a collar 707. The locking ring 705 can be employed to secure the telescoping shaft 702a at a desired amount of distraction. The collar 707 can be configured to allow an instrument to be attached to the interspinous implant 700 for the manipulation (lock, unlock) of the locking ring 705.

Figure 46:
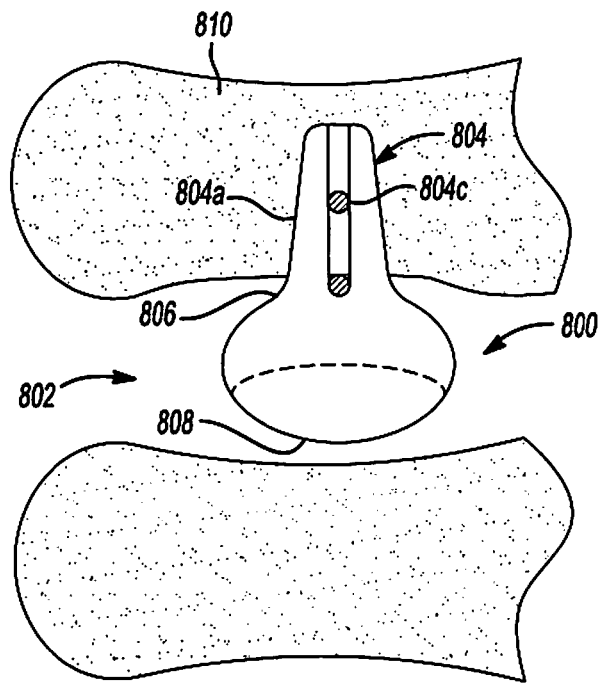
FIG. 46 is a schematic illustration of an exemplary interspinous implant according to various teachings.

As a further example, while the interspinous implant 100 has been described herein as having a first extension and a second extension, those of skill in the art will appreciate that the present disclosure, in its broadest aspects, may be constructed somewhat differently. In this regard, with reference to FIGS. 46 and 47, an interspinous implant 800 can include a body 802 and a first extension 804. The body 802 can have a first end 806 and a second end 808. The first end 806 can be coupled to the first extension 804, and the second end 808 can be configured to cooperate with an opposing spinous process.

Figure 47:
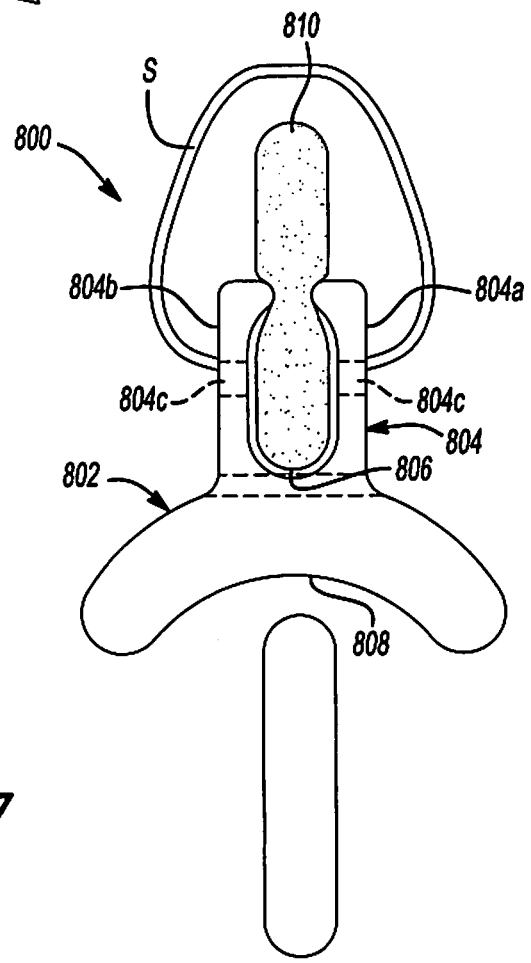
FIG. 47 is a front environmental view of the interspinous implant of FIG. 46.

In this regard, in one example, as shown in FIG. 47, the second end 808 of the body 802 can comprise a generally inverse U-shape, which can enable the second end 808 of the body 802 to cooperate with the opposing spinous process. In this regard, the body 802 can be spaced apart from the spinous process during flexion, and can contact the opposing spinous process during extension to restrict further movement.

Figure 48:
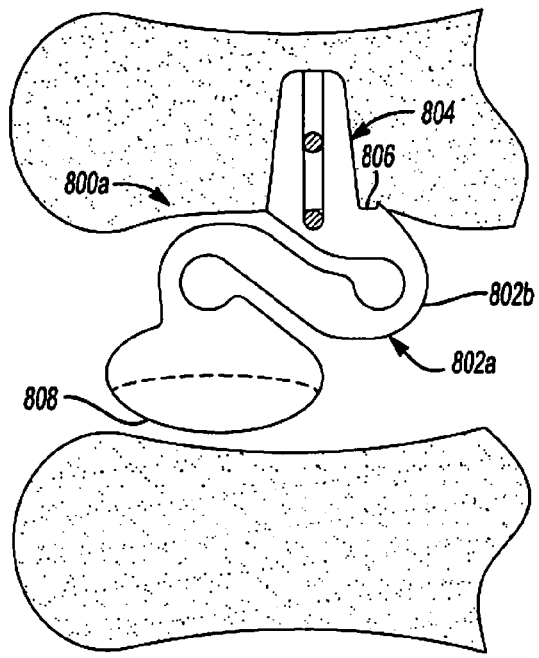
FIG. 48 is a schematic illustration of an exemplary interspinous implant according to various teachings.

It should be noted, however, that the body 802 can have any desired shape. For example, with brief reference to FIG. 48, an interspinous implant 800a can include a body 802a, which can have a generally S-shaped intermediate portion 802b and a generally inverse U-shaped second end 808. The generally S-shaped intermediate portion 802b can allow the body 802a to act as a tension spring to reduce loads in the disc space, as discussed previously.

With reference back to FIGS. 46 and 47, the first extension 804 can be coupled to the first end 806 of the body 802, and can generally be integrally formed with the body 802. It should be noted that the first extension 804 could be modularly coupled to the body 802 if desired, through a suitable technique discussed previously herein. With reference to FIG. 47, the first extension 804 can extend from the body 802 in a generally U-shape, and can have arms 804a, 804b. The arms 804a, 804b can be spaced apart to receive at least a portion of a spinous process 810 therein. In addition, the arms 804a, 804b can be coupled to the spinous process 810.

In this regard, the first extension 804 can couple or secure the interspinous implant 800 to the anatomy. In one example, the arms 804a, 804b can include at least one aperture 804c, which can receive a suture or a cable S, to couple the first extension 804 to the spinous process 810. It should be noted, however, that the first extension 804 can be coupled to the spinous process 810 through any suitable technique, such as by using teeth formed on an interior surface of the arms 804a, 804b, a biocompatible adhesive applied to an interior surface of the arms 804a, 804b, a mechanical fastener extending through the arms 804a, 804b and the spinous process 810, etc.

Figure 49:
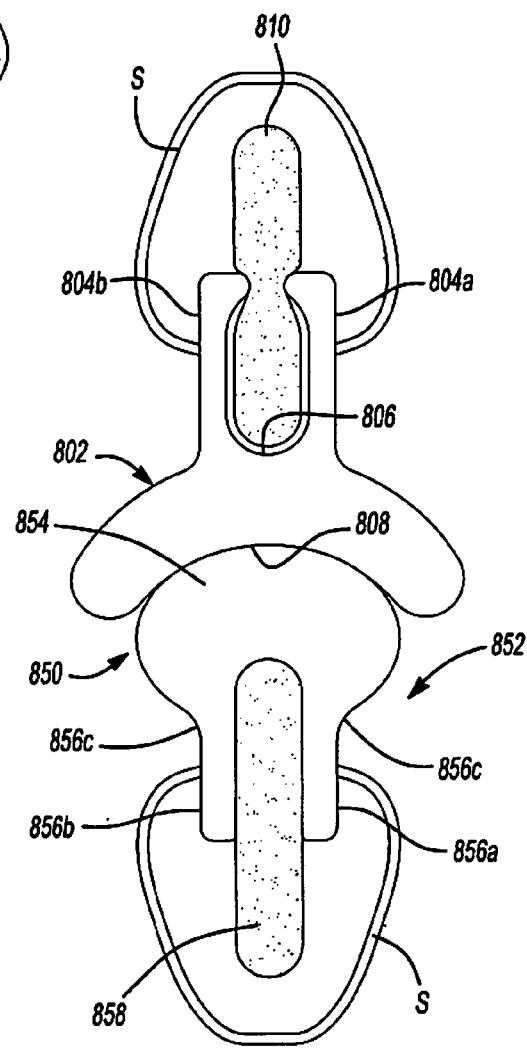
FIG. 49 is a schematic illustration of an exemplary interspinous implant according to various teachings.

As a further example, one of skill in the art will appreciate that a second body 850 could be movably coupled to the body 802 of the interspinous implant 800, as shown in FIG. 49. In this example, the second body 850 can have a first end 852 and a second end 854. The first end 852 can be coupled to a second extension 856, and the second end 854 can be configured to cooperate with an opposing spinous process.

The second extension 856 can be coupled to the first end 852 of the second body 850, and can generally be integrally formed with the second body 850. It should be noted that the second extension 856 could be modularly coupled to the second body 850 if desired, through a suitable technique discussed previously herein. The second extension 856 can extend from the second body 850 in a generally U-shape, and can have arms 856a, 856b. The arms 856a, 856b can be spaced apart to receive at least a portion of a spinous process 858 therein. In addition, the arms 856a, 856b can be coupled to the spinous process 858.

In this regard, the second extension 856 can couple or secure the second body 850 to the anatomy. In one example, the arms 856a, 856b can include at least one aperture 856c, which can receive a suture or a cable S, to couple the second extension 856 to the spinous process 858. It should be noted, however, that the second extension 856 can be coupled to the spinous process 858 through any suitable technique, such as by using teeth formed on an interior surface of the arms 856a, 856b, a biocompatible adhesive applied to an interior surface of the arms 856a, 856b, a mechanical fastener extending through the arms 856a, 856b and the spinous process 858, etc.

The second end 854 of the second body 850 can comprise a generally spherical bulb, which can be configured to movably engage the inverse U-shape of the second end 808 of the body 802 to enable relative movement, constrained or unconstrained, between the body 802 and the second body 850.

What is claimed:

1. An interspinous implant defining a longitudinal axis comprising:
    a main body including a first end and a second end at opposite sides of the main body, the first end defining a first coupling member;
    a first U-shaped portion and a second U-shaped portion of the main body defining a first channel and a second channel respectively, the first channel is between the first end and the second channel, the second channel is between the first channel and the second end, the first and the second channels extend parallel to each other and oblique to the longitudinal axis of the implant along at least portions of respective lengths thereof;
    an intermediate portion of the main body extending from the first U-shaped portion to the second U-shaped portion to join the first and the second U-shaped portions together in an offset relationship, the intermediate portion is between the first and the second channels to define a wall of each one of the first and the second channels, and including a first thickness that is greater than both a second thickness of the first U-shaped portion and a third thickness of the second U-shaped portion as measured along a transverse axis extending across the intermediate portion from the first U-shaped portion to the second U-shaped portion;
    a first extension defining a first opening between a first pair of opposing legs adapted to engage a first spinous process, the first extension including a first mating member configured to cooperate with the first coupling member to connect the first extension to the main body at the first end;
    a second extension at the second end of the main body and defining a second opening between a second pair of opposing legs and adapted to engage a second spinous process.

2. The interspinous implant of claim 1, wherein the first extension and the second extension are substantially U-shaped.

3. The interspinous implant of claim 1, wherein the first pair of opposing legs are tapered towards each another.

4. The interspinous implant of claim 1, wherein the first coupling member and the first mating member are tapered surfaces configured to couple with one another to connect the first extension to the main body.

5. The interspinous implant of claim 1, wherein the first extension is offset from the second extension with respect to the longitudinal axis and the first and second extensions are on opposite sides of the longitudinal axis.

6. The interspinous implant of claim 1, wherein the transverse axis is perpendicular to the longitudinal axis.

7. The interspinous implant of claim 1, wherein the second end of the main body defines a second coupling member and the second extension includes a second mating member configured to cooperate with the second coupling member to connect the second extension to the main body at the second end.

8. An interspinous implant defining a longitudinal axis comprising:
a main body including a first end and a second end at opposite sides of the main body, the first end defining a first coupling member and the second end defining a second coupling member, the main body is generally s-shaped;
a first U-shaped extension adapted to engage a first spinous process and including a first mating member configured to cooperate with the first coupling member to connect the first U-shaped extension to the main body at the first end; and
a second U-shaped extension adapted to engage a second spinous process and including a second mating member configured to cooperate with the second coupling member to connect the second U-shaped extension to the main body at the second end;
wherein the first and the second U-shaped extensions are laterally offset and on opposite sides of the longitudinal axis when coupled to the main body; and
wherein the body defines a first channel between the first end and an intermediate portion and a second channel between the second end and the intermediate portion, the intermediate portion serving as a border between the first and the second channels, the first and the second channels extend parallel to one another and oblique to the longitudinal axis along at least portions of respective lengths thereof.

9. An interspinous implant defining a longitudinal axis comprising:
a body having a first end generally opposite to a second end, the first end defining a first coupling member and the second end defining a second coupling member;
an intermediate portion of the main body between the first end and the second end, the intermediate portion extends lengthwise across the longitudinal axis;
a first U-shaped portion and a second U-shaped portion of the main body at opposite ends of the intermediate portion and aligned along a body axis extending perpendicular to, and transverse to, the longitudinal axis, the body axis extends through each of a first thickness of the first U-shaped portion, a second thickness of the second U-shaped portion, and a third thickness of the intermediate portion that is greater than each of the first and second thicknesses;
a first extension defining a first opening between a first pair of opposing legs adapted to engage a first spinous process, and including a first mating member configured to cooperate with the first coupling member to connect the first extension to the main body at the first end, the first extension is longitudinally aligned with the intermediate portion and longitudinally offset from each of the first and second U-shaped portions;
a second extension defining a second opening between a second pair of opposing legs adapted to engage a second spinous process, and including a second mating member configured to cooperate with the second coupling member to connect the second extension to the main body at the second end, the second extension is longitudinally aligned with the second U-shaped portion; and
a first channel defined by the implant between the intermediate portion and the first extension, and a second channel defined by the implant between the intermediate portion and the second extension, the first and second channels extend parallel to one another and oblique to the longitudinal axis along at least portions of respective lengths thereof.

10. The interspinous implant of claim 9, wherein the first extension and the second extension each define at least one aperture configured to receive a suture to retain the implant at the first and the second spinous processes.

11. An interspinous implant comprising:
a body including a first coupling portion and a second coupling portion on opposite sides of the body;
a first U-shaped extension including a first coupling member configured to cooperate with the first coupling portion to couple the first U-shaped extension to the body; and
a second U-shaped extension including a second coupling member configured to cooperate with the second coupling portion to couple the second U-shaped extension to the body; and
wherein the first and the second U-shaped extensions are laterally offset from a longitudinal axis of the implant and on opposite sides of the longitudinal axis; and
wherein the body defines a first channel and a second channel, the first channel is defined between the first coupling portion and the second channel, the second channel is defined between the first channel and the second coupling portion, the first and the second channels extend parallel to one another and oblique to the longitudinal axis along at least portions of respective lengths thereof.

12. The interspinous implant of claim 11, wherein between the first and the second coupling portions the body includes an intermediate portion, a first U-shaped portion on a first side of the intermediate portion, and a second U-shaped portion on a second side of the intermediate portion, the longitudinal axis extends across a width of the intermediate portion and the first and second U-shaped portion are on opposite sides of the longitudinal axis.

13. The interspinous implant of claim 12, wherein along a transverse axis extending transverse to the longitudinal axis, the first U-shaped portion includes a first thickness, the second U-shaped portion includes a second thickness, and the intermediate portion includes a third thickness that is greater than each of the first and the second thicknesses.

* * * * *